US009453797B2

(12) United States Patent
Geddes

(10) Patent No.: US 9,453,797 B2
(45) Date of Patent: Sep. 27, 2016

(54) METAL ENHANCED FLUORESCENCE FROM METALLIC NANOBURGER STRUCTURES

(71) Applicant: UNIVERSITY OF MARYLAND, BALTIMORE COUNTY, Baltimore, MD (US)

(72) Inventor: Chris D. Geddes, Bel-Air, MD (US)

(73) Assignee: UNIVERSITY OF MARYLAND, BALTIMORE COUNTY, Baltimore, MD (US)

(*) Notice: Subject to any disclaimer, the term of this patent is extended or adjusted under 35 U.S.C. 154(b) by 34 days.

(21) Appl. No.: 14/276,207

(22) Filed: May 13, 2014

(65) Prior Publication Data

US 2014/0287224 A1    Sep. 25, 2014

Related U.S. Application Data

(62) Division of application No. 13/511,718, filed as application No. PCT/US2010/057946 on Nov. 24, 2010, now Pat. No. 8,722,428.

(60) Provisional application No. 61/264,645, filed on Nov. 25, 2009.

(51) Int. Cl.
*G01N 33/543* (2006.01)
*G01N 33/553* (2006.01)
(Continued)

(52) U.S. Cl.
CPC .............. *G01N 21/64* (2013.01); *B82Y 15/00* (2013.01); *G01N 21/554* (2013.01); *G01N 21/6408* (2013.01); *G01N 21/648* (2013.01); *G01N 33/54346* (2013.01); *G01N 33/54353* (2013.01);
(Continued)

(58) Field of Classification Search
CPC ................ G01N 33/54346; G01N 33/54353; G01N 33/553; G01N 21/554
See application file for complete search history.

(56) References Cited

U.S. PATENT DOCUMENTS 6,579,721 B1    6/2003 Natan et al.
7,095,502 B2    8/2006 Lakowicz et al.
(Continued)

FOREIGN PATENT DOCUMENTS

JP    2006-349532    12/2006

OTHER PUBLICATIONS

Alfano, R. R. et al. Fluorescence-Spectra from Cancerous and Normal Human-Breast and Lung Tissues. *Ieee Journal of Quantum Electronics* 1987, 23, (10), 1806-1811.
(Continued)

*Primary Examiner* — Erik B Crawford
*Assistant Examiner* — Gary E Hollinden
(74) *Attorney, Agent, or Firm* — Marianne Fuierer; Moore & Van Allen, PLLC

(57) ABSTRACT

The present invention provides for metallic nanostructures or nanoburgers comprising a dielectric layer positioned between metallic layers and their use in metal enhanced emissions systems to enhance emissions from fluorophores, including intrinsic and extrinsic; luminophores; bioluminescent species and/or chemiluminescent species. The multi-layer nanoburgers exhibit several distinctive properties including significantly enhanced intensity of emissions, decreased lifetime and increased photostability by simply varying the thickness of the dielectric layer while maintaining a constant thickness of the two metallic layers on opposite sides of the dielectric layer.

4 Claims, 11 Drawing Sheets

(51) Int. Cl.
  G01N 21/55    (2014.01)
  G01N 21/64    (2006.01)
  B82Y 15/00    (2011.01)
  G01N 21/552   (2014.01)
(52) U.S. Cl.
  CPC .......... G01N 33/553 (2013.01); Y10T 428/256 (2015.01)

(56) References Cited

U.S. PATENT DOCUMENTS

| | | |
|---|---|---|
| 7,400,397 B2 | 7/2008 | Lakowicz et al. |
| 7,718,804 B2 | 5/2010 | Geddes et al. |
| 7,732,215 B2 | 6/2010 | Geddes et al. |
| 7,939,333 B2 | 5/2011 | Geddes et al. |
| 8,008,067 B2 | 8/2011 | Geddes et al. |
| 8,034,633 B2 | 10/2011 | Geddes |
| 8,075,956 B2 | 12/2011 | Geddes et al. |
| 8,101,424 B2 | 1/2012 | Geddes |
| 8,114,598 B2 | 2/2012 | Geddes et al. |
| 8,182,878 B2 | 5/2012 | Geddes et al. |
| 8,279,444 B2 | 10/2012 | Boukherroub et al. |
| 8,318,087 B2 | 11/2012 | Geddes |
| 8,338,602 B2 | 12/2012 | Geddes et al. |
| 8,697,434 B2 * | 4/2014 | Voorhees .................. 435/287.9 |
| 8,802,447 B2 * | 8/2014 | Swager et al. ............... 436/528 |
| 8,841,134 B2 * | 9/2014 | Papineni et al. ............. 436/172 |
| 9,005,890 B1 * | 4/2015 | Bhethanabotla et al. ..... 435/6.1 |
| 2003/0228682 A1 | 12/2003 | Lakowicz et al. |
| 2005/0053974 A1 | 3/2005 | Lakowicz et al. |
| 2005/0176029 A1 | 8/2005 | Heller et al. |
| 2005/0244977 A1 | 11/2005 | Drachev et al. |
| 2006/0034729 A1 | 2/2006 | Poponin |
| 2006/0269930 A1 | 11/2006 | Robotti et al. |
| 2006/0274315 A1 | 12/2006 | Saito |
| 2007/0141727 A1 | 6/2007 | Huang et al. |
| 2007/0269826 A1 | 11/2007 | Geddes |
| 2008/0038830 A1 | 2/2008 | Ure et al. |
| 2008/0215122 A1 | 9/2008 | Geddes |
| 2009/0022766 A1 | 1/2009 | Geddes |
| 2009/0045351 A1 | 2/2009 | Smolyaninov et al. |
| 2009/0128822 A1 | 5/2009 | Yamamichi et al. |
| 2009/0325199 A1 | 12/2009 | Geddes et al. |
| 2010/0149540 A1 | 6/2010 | Boukherroub et al. |
| 2010/0209937 A1 | 8/2010 | Geddes et al. |
| 2010/0264333 A1 | 10/2010 | Offermans et al. |
| 2011/0020946 A1 | 1/2011 | Geddes |
| 2011/0046018 A1 | 2/2011 | Chen et al. |
| 2011/0136154 A1 | 6/2011 | Geddes |
| 2011/0207236 A1 | 8/2011 | Geddes |
| 2012/0021443 A1 | 1/2012 | Geddes |
| 2012/0028270 A1 | 2/2012 | Geddes |
| 2012/0091349 A1 | 4/2012 | Geddes |
| 2012/0107952 A1 | 5/2012 | Geddes et al. |
| 2012/0142552 A1 | 6/2012 | Geddes et al. |
| 2012/0238035 A1 | 9/2012 | Geddes |
| 2012/0282630 A1 | 11/2012 | Geddes |

OTHER PUBLICATIONS

Andersson, H. et al. Autofluorescence of living cells. *Journal of Microscopy-Oxford* 1998, 191, 1-7.
Aroca, R. et al. Fluorescence Enhancement from Langmuir-Blodgett Monolayers on Silver Island Films. *Langmuir* 1988, 4, (3), 518-521.
Aslan, K. et al. Angular-dependent metal-enhanced fluorescence from silver colloid-deposited films: opportunity for angular-ratiometric surface assays. *Analyst* 2007, 132, (11), 1112-1121.
Aslan, K. et al. Metal-enhanced fluorescence from gold surfaces: angular dependent emission. *J Fluoresc* 2007, 17, (1), 7-13.
Aslan, K. et al. Metal-enhanced fluorescence from plastic substrates. *Journal of Fluorescence* 2005, 15, (2), 99-104.
Aslan, K. et al. Metal-enhanced fluorescence solution-based sensing platform. *Journal of Fluorescence* 2004, 14, (6), 677-679.
Aslan, K. et al. Annealed silver-island films for applications in metal-enhanced fluorescence: Interpretation in terms of radiating plasmons. *Journal of Fluorescence* 2005, 15, (5), 643-654.
Aslan, K. et al. Metal-Enhanced Fluorescence from Nanoparticulate Zinc Films. *Journal of Physical Chemistry C.* 2008, 112, (47), 18368-18375.
Chance, R. R. et al. Fluorescence and Energy-Transfer near Interfaces—Complete and Quantitative Description of Eu+3-Mirror Systems. *Journal of Chemical Physics* 1975, 63, (4), 1589-1595.
Chen, Y. et al. Dependence of fluorescence intensity on the spectral overlap between fluorophores and plasmon resonant single silver nanoparticles. *Nano Letters* 2007, 7, (3), 690-696.
Cheng, P. P. et al. Dynamic and static quenching of fluorescence by 1-4 nm diameter gold monolayer-protected clusters. *J Phys Chem B Condens Matter Mater Surf Interfaces Biophys* 2006, 110, (10), 4637-44.
Chowdchury, S. et al. Silver-copper alloy nanoparticles for metal enhanced luminescence. *Applied Physics Letters* 2009, 95, (13), 1311-15.
Croce, A. C. et al. Autofluorescence properties of isolated rat hepatocytes under different metabolic conditions. *Photochemical & Photobiological Sciences* 2004, 3, (10), 920-926.
Cullum, M. E. et al. Diagnosis of militarily relevant diseases using oral fluid and saliva antibodies: fluorescence polarization immunoassay. *Mil Med* 2003, 168, (11), 915-21.
Davidson, R. S. et al. The Use of Fluorescent-Probes in Immunochemistry. *Photochemistry and Photobiology* 1990, 52, (2), 431-438.
Doron, A. et al. Organization of Au Colloids as Monolayer Films onto Ito Glass Surfaces—Application of the Metal Colloid Films as Base Interfaces to Construct Redox-Active Monolayers. *Langmuir* 1995, 11, (4), 1313-1317.
Dostalek, J. et al. Biosensors based on surface plasmon-enhanced fluorescence spectroscopy. *Biointerphases* 2008, 3, (3), FD12.
Drexhage, K. H., Influence of a dielectric interface on fluorescence decay time. *J. Luminesc* 1970, 1/2, 693-701.
Enderlein, J. et al. Highly efficient optical detection of surface-generated fluorescence. *Applied Optics* 1999, 38, (4), 724-732.
Garoff, S. et al. Optical-Absorption Resonances of Dye-Coated Silver-Island Films. *Optics Letters* 1981, 6, (5), 245-247.
Garrett, S. et al. Fluorescence in the presence of metallic hole arrays. *Journal of Modern Optics* 2005, 52, (8), 1105.
Geddes, C. D. et al. Metal-enhanced fluorescence. *Journal of Fluorescence* 2002, 12, (2), 121-129.
Gersten, J. I., *Theory of fluorophore-metallic surface interactions*. Springer: New York, 2004; vol. 8, p. 197-221.
Kasry, A. et al. Long range surface plasmon fluorescence spectroscopy. *Applied Physics Letters* 2006, 89, (10), 101106.
Kawasaki, M. et al. Enhanced molecular fluorescence near thick Ag island film of large pseudotabular nanoparticles. *Journal of Physical Chemistry B* 2005, 109, (36), 17254-17261.
Kummerlen, J. et al. Enhanced Dye Fluorescence over Silver Island Films—Analysis of the Distance Dependence. *Molecular Physics* 1993, 80, (5), 1031-1046.
Lakowicz, J. R. Radiative decay engineering: Biophysical and biomedical applications. *Analytical Biochemistry* 2001, 298, (1), 1-24.
Lakowicz, J. R. Radiative decay engineering 5: metal-enhanced fluorescence and plasmon emission. *Analytical Biochemistry* 2005, 337, (2), 171-194.
Malicka, J. et al. Metal-enhanced emission from indocyanine green: a new approach to in vivo imaging. *J Biomed Opt* 2003, 8, (3), 472-8.
Praharaj, S. et al. Size-selective systhesis and stabluzation of gold organosol in CnTAC:Enhanced molucular fluorescence from gold-bound fluorophores. *Journal of physical Chemistry B* 2005, 109, (27), 13166.
Pribik, R. et al. Metal-Enhanced Fluorescence from Chromium Nanodeposits. *Journal of Physical Chemistry C.*, 2008, 112, 17969-17973.

(56) References Cited

OTHER PUBLICATIONS

Stefani, F. et al. Surface-plasmon-mediated single-molecule fluorescence throhgh a thin metallic film. *Physical Review Letters* 2005, 94, (2).

Stranik, O. et al. Plasmonic enhancement of fluorescence for sensor applications. *Sensors and Actuators B-Chemical* 2005, 107, (1), 148.

Wei, Q.H. et al. Engineering "hot spots" for surface enhanced raman scattering. Proceedings of SPIE (2003) 5221:92-99.

Zhang, Y. et al. Metal-enhanced fluorescence from copper substrates. *Applied Physical Letters* 2007, 90, (17), 173116.

Zhang, Y. et al. Wavelength—Dependence of Metal-Enhanced Fluorescence. *Journal of Physical Chemistry C.* 2009, 113 12095-12100.

Zhang, Y. et al. Near-Infrared Metal-Enhanced Fluorescence Using Nickel Nanodeposits. *submitted to Journal of Physical Chemistry C* 2009.

Zhang, Y. et al. Metal-Enhanced Fluorescence from Tin nanostructured Surfaces *Accepted by Journal of Applied Physics* 2009.

Zhang, Y. et al. Interactions of the Fluorophores with Iron Nanoparticles: Metal—Enhanced Fluorescence *submitted to the Journal of Physical Chemistry C* 2010.

\* cited by examiner (a)

(b)

(a)

(b)

(e)

(f)

METAL ENHANCED FLUORESCENCE FROM METALLIC NANOBURGER STRUCTURES

CROSS-REFERENCE TO RELATED APPLICATIONS

This application is a divisional application of U.S. patent application Ser. No. 13/511,718 now U.S. Pat. No. 8,722,428 which was filed under the provisions of 35 U.S.C. §371 and claimed priority of International Patent Application No. PCT/US2010/057946 filed on Nov. 24, 2010, which in turn claimed priority to U.S. Provisional Patent Application No. 61/264,645 filed on Nov. 25, 2009, the contents of which are hereby incorporated by reference herein for all purposes.

BACKGROUND OF THE INVENTION

1. Field of the Invention

The present invention relates to metallic nanostructures, and more particularly, to layered structures comprising a dielectric material layer positioned between metallic layers and their use in metal enhanced emissions systems to enhance emissions from fluorophores, including intrinsic and extrinsic fluorophores; luminophores; bioluminescent species and/or chemiluminescent species.

2. Background of the Related Art

Fluorescence detection is an important tool in medical diagnostics high-throughput screening, microscopy and indeed biotechnology today.[1-5] While fluorescence spectroscopy displays exquisites sensitivity,[2,6,7] the detection limit is usually limited by the quantum yield of the fluorophore (label), the autofluorescence of the sample and the photostability of the fluorophores, which are fundamentally far-field fluorescence properties.[8] In this regard, metallic nanostructures[9-12] have been used to favorably modify the spectral properties of fluorophores and to alleviate some of their more classical photophysical far-field constraints.[13-23] The use of fluorophore-metal interactions has been termed Metal-Enhanced Fluorescence (MEF) by Geddes.[24] To date, MEF from plasmonic nanostructured materials such as Silver,[25,26] Gold,[27] Copper,[28] Zinc,[29] Chromium,[30] Nickel,[31] Tin,[32] and Iron,[33] have been observed. In this regard, silver island films (SIFs) have been popular substrates used for applications of MEF for fluorophores emitting in the visible wavelength region.

However, these studies have for the most part been focused on one SIF layer[14, 34-36] and thus provide no ability to provide different layer sizes or components within such layers to provide tunable responses from the SIFs. Thus, it would advantageous to provide multiple layers of such metallic particles with a metallic oxide layer positioned therebetween to provide increased intensity of emissions and photostability.

SUMMARY OF THE INVENTION

The present invention provides for structures of metallic nanoparticle layer/dielectric layer/metal metallic nanoparticle layer that exhibit several distinctive properties including significantly enhanced intensity of fluorescence, decreased lifetime and increased fluorophore photostability. Notably, dielectric materials may include any material that acts as an insulator, restricts movement of electrons therewithin and preferably has a dielectric constant greater than three (3). Such dielectrics may include solid materials such as metal oxides; organic polymers such as epoxy and nylon, polyvinyl chloride (pvc);

The thickness of the metal oxide, dielectric layer or optical coating can be varied while maintaining the consistency of the metallic particle layers thereby providing an electric field intensity that can be tuned by varying the distance between the metallic particles.

The metallic particles may be fabricated from any metal that conducts and/or has the ability to support plasmonic interactions including Silver, Gold, Aluminium, Zinc, Rhodium, Copper, Nickel, Palladium, Indium, Tin, Iron, Tungsten, Platinum or Germanium, and combinations thereof.

In one aspect the present invention provides a substrate comprising metalized structures, wherein the metalized structures comprise two metalized layers with a metal oxide layer positioned therebetween. Preferably, the metal oxide layer positioned between the two metallic layers has a thickness from about 2 nm to about 15 nm, more preferably from about 5 nm to about 10 nm, and most preferably from about 6 nm to about 8 nm.

In another aspect, the present invention provides for a metalized structure comprising a layer structure comprising a silver island film/$SiO_2$/silver island film. The metalized structure can be free in solution or connected to a substrate.

In yet another aspect, the present invention provides for a detection system, the system comprising:
  a) a substrate comprising a multiplicity of metallic structures, wherein the metallic structures comprise two metalized layers with a dielectric material layer positioned therebetween;
  b) at least one excitable molecule that is positioned near at least one of the metalized layer of the metallic structure material in a range from about 5 nm to 50 nm, wherein the excitable molecule is selected from the group of an intrinsic fluorophore, extrinsic fluorophore, fluorescent dye and luminophores,
  c) a source of electromagnetic energy for providing excitation energy to excite the molecule; and
  d) a detector for detecting emissions from the excited molecule and/or the metallic structure.

In a still further aspect the present invention provides for a detection system, the system comprising:
  a) a substrate comprising a multiplicity of metallic structures, wherein the metallic structures comprise two metalized layers with a metal oxide layer positioned therebetween, wherein the metal oxide layer has a thickness from about 2 nm to about 15 nm and more preferably from about 5 nm to 10 nm;
  b) at least one excitable molecule that is positioned near at least one of the metalized layers of the metallic structure in a range from about 5 nm to 50 nm, wherein the excitable molecule is one molecule involved in a chemiluminescence or bioluminescence reaction;
  c) a binding molecule that binds to the excitable molecule and such binding causes a chemical reactions that emits energy; and
  d) a detector for detecting emissions from the excited molecule and/or the metallic structure.

The emission enhancement may be observed when the fluorophore, luminophores; bioluminescent species or chemiluminescent species is positioned from about 5 nm to about 200 nm to metal surfaces. Preferable distances are about 5 nm to about 30 nm, and more preferably, 5 nm to about 20 nm to metal surfaces.

Another aspect of the invention relates to a method of enhancing emissions from fluorescence, chemiluminescence, bioluminescence, and luminescence molecules and reactions that exhibit emissions in wavelengths from UV-visible to near IR.

The present invention relates to a method of detection using plasmonic emissions from metallic surfaces caused by fluorescence, chemiluminescence or bioluminescence based reactions. These plasmonic emissions emitted from metallic surface plasmons are generated either with an external excitation or a chemical reaction that induces electronically excited states.

In yet another aspect, the present invention relates to a method of metal-enhanced fluorescence sensing, comprising:
  a) applying metallic structures comprising two metalized layers with a metal oxide layer positioned therebetween to a surface used in a detection system;
  b) introducing a solution containing at least one biomolecule for disposing near the metallic structures, wherein the biomolecule is capable of a chemically induced electronically excited state;
  c) triggering the chemically induced electronically excited state of the biomolecule; and
  d) measuring the bioluminescent or chemiluminescent intensity.

In yet another aspect, the present invention relates to a method for detecting a target molecule in a sample, the method comprising:
  a) providing a system comprising:
    (i) a layer of immobilized metallic structures comprising two metalized layers with a metal oxide layer positioned therebetween positioned on a surface substrate, wherein the immobilized metallic structures have attached thereto a captured biomolecular probe with an affinity for the target molecule; and
    (ii) a free biomolecular probe with an affinity for the target molecule, wherein the free biomolecular probe has attached thereto a fluorophore;
  b) contacting the sample with the immobilized biomolecular probes, wherein the target molecules binds to the immobilized biomolecular probes; and
  c) contacting the bound target molecule with the free biomolecular probe, wherein binding of the free biomolecular probe to the target molecule causes the fluorophore to be positioned a sufficient distance from the immobilized metallic structures to enhance fluorescence emission when excited by an irradiating source.

The metallic layers may be fabricated from any metal including silver, gold, platinum, aluminum, copper, zinc, chromium, nickel, tin, iron, palladium and composites thereof. Notably, the different layers can be fabricated from two distinctly different metals. The substrate positioned beneath the metallic structures may include glass, a cellulosic material and/or a polymeric material.

If the dielectric layer is a metal oxide layer, such oxide layer may be formed from a deposition technique, such as vapor deposition. The oxide layer may include at least one metal selected from the group consisting of Al, Ca, Ti, Fe, Cu, Zn, Y, Zr, Nb, Mo, In, Si, Sn, Sb, Ta, W, Pb, Bi and Ce and having a valence of from 2 to 6. The form of the oxide of such a metal may, for example, be $Al_2O_3$, $SiO_2$, $TiO_2$, $Fe_2O_3$, $CuO$, $ZnO$, $Y_2O_3$, $ZrO_2$, $Nb_2O_5$, $MoO_3$, $In_2O_3$, $SnO_2$, $Sb_2O_5$, $Ta_2O_5$, $WO_3$, $PbO$ or $Bi_2O_3$. These metal oxides may be used alone or in combination with other types of coatings. Preferably, the oxide is a silicon oxide, more preferably, $SiO_2$. The vapor deposition of $SiO_2$ is a well established technique for the controlled deposition of a variety of substrates. For example, an Edwards Vapor deposition module allows the deposition of an inert coating of $SiO_2$.

The dielectric layer may further include other types of materials including metallic compounds such as calcite, mica, calcium carbonate, $MgF_2$, $CaF_2$, diamond, germanium, lead titanate, lithium deuteride, silicon carbide; polymeric materials including epoxy, nylon, plexiglass, polyvinyl chloride, and polyester.

A still further aspect of the invention relates to a bioassay for measuring concentration of receptor-ligand binding in a test sample, the method comprising:
  a) preparing metallic structures of the present invention immobilized on a surface wherein the metallic structures have positioned thereon a receptor molecule having affinity for a ligand of interest;
  b) contacting the receptor molecule with the test sample suspected of comprising the ligand of interest, wherein the ligand of interest will bind to the receptor molecule to form a receptor-ligand complex;
  c) contacting the receptor-ligand complex with a detector molecule having affinity for the ligand to form a receptor-ligand-detector complex, wherein the detector molecule comprises a first component of a bioluminescence or chemiluminescence generating system;
  d) exposing the first component of the bioluminescence or chemiluminescence generating system to a trigger solution comprising a second component that will chemically react with the first component to induce a chemically electronically excited state; and
  e) measuring the intensity of radiation emitted from exited metallic surface plasmons and/or test sample.

Preferably, the components of the bioluminescence generating system are a luciferase and a luciferin. The bioluminescence generating system may be selected from the group consisting of those isolated from the ctenophores, coelenterases, mollusca, fish, ostracods, insects, bacteria, a crustacea, annelids, and earthworms. The luciferase may be selected from the group consisting of Aequorea, Vargula, Renilla, Obelin, Porichthys, Odontosyllis, Aristostomias, Pachystomias, firefly, and bacterial systems.

In another aspect the present invention relates to a system for generating electrical current, the system comprising:
  i. a substrate comprising metallic structures comprising two metalized layers with a metal oxide layer positioned therebetween, wherein the metallic structures are at least partially covered with a polar solution;
  ii. a set of electrodes communicatively contacting at least some of the metallic structures positioned thereon; and
  iii. an intrinsic or extrinsic fluorophore positioned near the metallic structures, wherein when the fluorophore is excited by electromagnetic energy a mirror dipole is induced in the metallic structures causing plasmonic current flow for storage, directing to a current reading device or to provide sufficient amperage to power a device.

In yet another aspect, the present invention relates to a biosensing method for measuring concentration of an analyte that induces aggregation of metallic structures, the method comprising:
  a) preparing the metallic structures comprising two metalized layers with a metal oxide layer positioned therebetween, wherein the metallic structures are coated with a binding component having an affinity for the analyte, and wherein the metallic structures are at size that scatters light according to the Rayleigh theory;

b) exposing the metallic structures with electromagnetic radiation at a frequency that is at least scattered by the metallic structures;
c) measuring the polarization of scattered light from the metallic structures;
d) contacting the metallic nanostructures with an analyte that has an affinity for the binding component; and
e) measuring the polarization of scattered light emitted from the metallic structures, wherein the polarization decreases as aggregation increases.

In a still further aspect, the present invention relates to an assay using High Throughput Screening (HTS), the method comprising:
a) providing a well plate used in HTS systems comprising a multiplicity of wells;
b) introducing metallic structures into the wells, wherein the metallic structures comprise two metalized layers with a metal oxide layer positioned therebetween and are coupled to a binding receptor having affinity for a target molecule;
c) introducing at solution suspected of including the target molecule for binding to the binding receptor;
d) applying electromagnetic energy; and
e) measuring the change of polarization of plasmonic emissions from the system during a predetermined time period, wherein polarization values decrease as the binding of the target molecule increases.

Notably, all of the above discussed systems and methods may be further contacted with low power microwave energy or ultrasonic energy in an amount that increases a chemical or binding reaction within the systems.

Other aspects and advantages of the invention will be more fully apparent from the ensuing disclosure and appended claims.

DETAILED DESCRIPTION OF THE INVENTION

Figure 1:
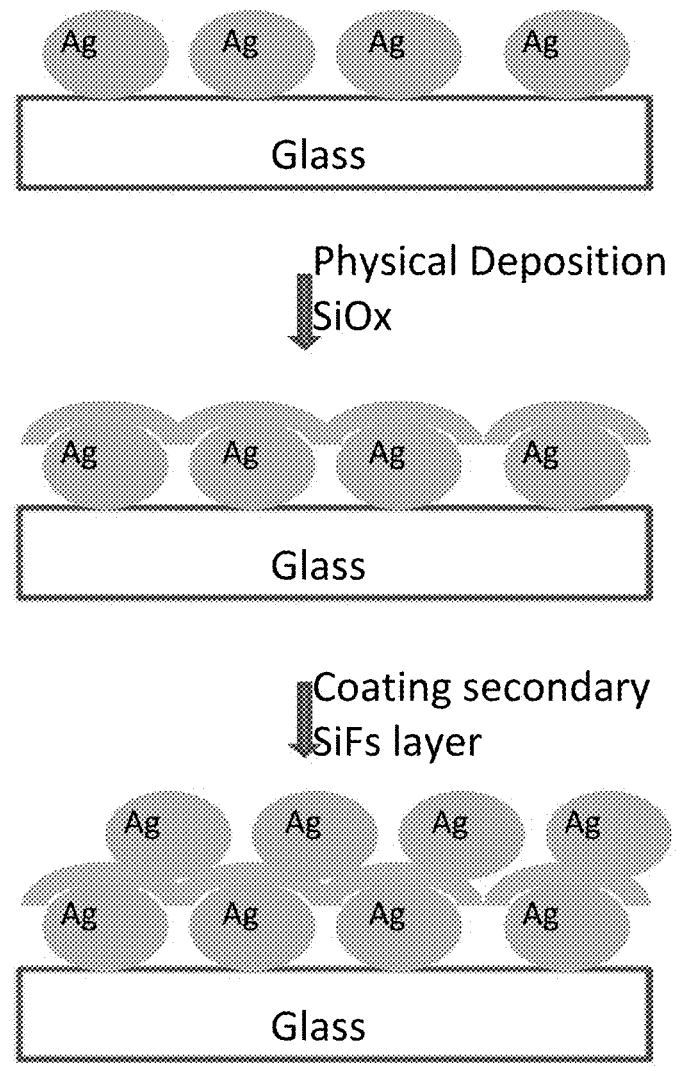
FIG. 1 shows the process of the nanoburger surface preparation

Before the present invention is disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural references unless the content clearly dictates otherwise.

The term "biomolecule" means any carbon based molecule occurring in nature or a derivative of such a molecule. The biomolecule can be in active or inactive form. "Active form" means the biomolecule is in a form that can perform a biological function. "Inactive form" means the biomolecule must be processed either naturally or synthetically before the biomolecule can perform a biological function. Exemplary biomolecules include nucleic acids, aromatic carbon ring structures, NADH, FAD, amino acids, carbohydrates, steroids, flavins, proteins, DNA, RNA, oligonucleotides, peptide nucleic acids, fatty acids, sugar groups such as glucose etc., vitamins, cofactors, purines, pyrimidines, formycin, lipids, phytochrome, phytofluor, peptides, lipids, antibodies and phycobiliproptein.

Fluorophore," and "fluorescence label," used interchangeably herein, means any substance that emits electromagnetic energy such as light at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals. Additionally fluorophore includes both extrinsic and intrinsic fluorophores. Extrinsic fluorophore refer to fluorophores bound to another substance. Intrinsic fluorophores refer to substances that are fluorophores themselves. Exemplary fluorophores include but are not limited to those listed in the Molecular Probes Catalogue which is incorporated by reference herein.

Representative fluorophores include but are not limited to Alexa Fluor® 350, Dansyl Chloride (DNS-Cl), 5-(iodoacetamida)fluoroscein (5-IAF); fluoroscein 5-isothiocyanate (FITC), tetramethylrhodamine 5- (and 6-)isothiocyanate (TRITC), 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, 5-carboxyrhodamine 6G hydrochloride, Lissamine rhodamine B sulfonyl chloride, Texas Red™. sulfonyl chloride, BODIPY™, naphthalamine sulfonic acids including but not limited to 1-anilinonaphthalene-8-sulfonic acid (ANS) and 6-(p-toluidinyl) naphthalen-e-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3- sulfonatopropyl)-4-[-.beta.-[2[(di-n-butylamino)-6 naphthyl]vinyl]pyridinium betaine (Naphtyl Styryl), 3,3'dipropylthiadicarbocyanine (diS-$C_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1,4',6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, and metal-ligand complexes.

Representative intrinsic fluorophores include but are not limited to organic compounds having aromatic ring structures including but not limited to NADH, FAD, tyrosine, tryptophan, purines, pyrimidines, lipids, fatty acids, nucleic acids, nucleotides, nucleosides, amino acids, proteins, peptides, DNA, RNA, sugars, and vitamins. Additional suitable fluorophores include enzyme-cofactors; lanthanide, green fluorescent protein, yellow fluorescent protein, red fluorescent protein, or mutants and derivates thereof.

Fluorophores with high radiative rates have high quantum yields and short lifetimes. Increasing the quantum yield requires decreasing the non-radiative rates $k_{nr}$, which is often only accomplished when using a low solution temperature or a fluorophore bound in a more rigid environment. The natural lifetime of a fluorophore, $\tau_n$, is the inverse of the radiative decay rate or the lifetime which would be observed if their quantum yields were unity. This value is determined by the oscillator strength (extinction coefficient) of the electronic transition. Hence, for almost all examples currently employed in fluorescence spectroscopy, the radiative decay rate is essentially constant. The modification and control of the radiative rate have also been referred as Radiative Decay Engineering (RDE), or "lightening rod" fluorescence enhancement effect. For example, enhanced intrinsic DNA fluorescence above metallic particles has recently been observed, which is typically not readily observable because of DNA's very low quantum yield of less than $10^{-4}$. The second favorable "lightening rod" effect also increases the fluorescence intensity by locally enhanced excitation. In this case, emission of fluorophores can be substantially enhanced irrespective of their quantum yields.

The reduction in lifetime of a fluorophore near a metal is due to an interaction between the fluorophore and metal particle, which enhances the radiative decay rate (quantum yield increase) or depending on distance, $d^{-3}$, causes quenching. It should be noted that lifetimes of fluorophores with high quantum yields (0.5) would decrease substantially more than the lifetimes of those with low quantum yields (0.1 and 0.01). A shorter excited-state lifetime also allows less photochemical reactions, which subsequently results in an increased fluorophore photostability. Notably, the use of low quantum yield fluorophores would lead to much larger fluorescence enhancements (i.e. $1/Q_0$) and could significantly reduce unwanted background emission from fluorophores distal from the silvered assay.

Fluorophore photostability is a primary concern in many applications of fluorescence. This is particularly true in single molecule spectroscopy. A shorter lifetime also allows for a larger photon flux. The maximum number of photons that are emitted each second by a fluorophore is roughly limited by the lifetime of its excited state. For example, a 10 ns lifetime can yield about $10^8$ photons per second per molecule, but in practice, only $10^3$ photons can be readily observed. The small number of observed photons is typically due to both photo-destruction and isotropic emission. If a metal surface decreases the lifetime, one can obtain more photons per second per molecule by appropriately increasing the incident intensity.

On the other hand, the metal-enhanced fluorescence provides enhanced intensity, while simultaneously shortening the lifetime. That is, it may be possible to decrease the excitation intensity, yet still see a significant increase in the emission intensity and photostability.

The emission enhancement may be observed at distances according to the type of fluorophore to be detected and the type, shape of the metal material, noting a difference between a film and a metallic island or colloid. For example, emission enhancement may be observed when a fluorophore is positioned from about 5 nm to about 200 nm from the metal surfaces. Preferable distances are about 5 nm to about 30 nm, and more preferably, 5 nm to about 20 nm to metal surfaces. At this scale, there are few phenomena that provide opportunities for new levels of sensing, manipulation, and control. However, the present invention leads to dramatically enhanced performance, sensitivity, and reliability with dramatically decreased size, weight, and therefore cost.

Attaching of the fluorophore to a probe may be achieved by any of the techniques familiar to those skilled in the art. For example, the fluorophore may be covalently attached to the bimolecular probe by methods disclosed in U.S. Pat. No. 5,194,300 (Cheung) and U.S. Pat. No. 4,774,189 (Schwartz).

In another embodiment, the assay system of the present invention provides for detecting and separating at least two target pathogen by choosing fluorophores such that they possess substantially different emission spectra, preferably having emission maxima separated by greater than 10 nm, more preferably having emission maxima separated by greater than 25 nm, even more preferably separated by greater than 50 nm. When differentiation between the two fluorophores is accomplished by visual inspection, the two dyes preferably have emission wavelengths of perceptibly different colors to enhance visual discrimination. When it is desirable to differentiate between the two fluorophores using instrumental methods, a variety of filters and diffraction gratings allow the respective emission maxima to be independently detected.

Any chemiluminescent species may be used in the present invention that provides for a chemical reaction which produces a detectable reaction (observed emission) wherein the excited state responsible for the observed emission including, but not limited to the following excitation mechanisms:

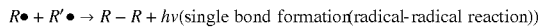

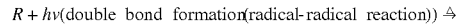

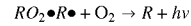

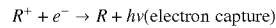

Examples of suitable chemiluminescence detector molecules include but without limitation, peroxidase, bacterial luciferase, firefly luciferase, functionalized iron-porphyrin derivatives, luminal, isoluminol, acridinium esters, sulfonamide and others. A recent chemiluminescent label includes xanthine oxidase with hypoxanthine as substrate. The triggering agent contains perborate, a Fe-EDTA complex and luminol. Choice of the particular chemiluminescence labels depends upon several factors which include the cost of preparing labeled members, the method to be used for covalent coupling to the detector molecule, and the size of the detector molecules and/or chemiluminescence label. Correspondingly, the choice of chemiluminescence triggering agent will depend upon the particular chemiluminescence label being used.

Chemiluminescent reactions have been intensely studied and are well documented in the literature. For example, peroxidase is well suited for attachment to the detector molecule for use as a chemiluminescence. The triggering agent effective for inducing light emission in the first reaction would then comprise hydrogen peroxide and luminol. Other triggering agents which could also be used to induce a light response in the presence of peroxidase include isobutyraldehyde and oxygen. Procedures for labeling detector molecules, such as antibodies or antigens with peroxidase are known in the art. For example, to prepare peroxidase-labeled antibodies or antigens, peroxidase and antigens or antibodies are each reacted with N-succinimidyl 3-(2-pyridyldithio) proprionate (hereinafter SPDP) separately. SPDP-labeled peroxidase, or SPDP-labeled antigen or antibody is then reacted with dithiothreitol to produce thiol-labeled peroxidase, or thiol-labeled antigen or antibody. The thiol derivative is then allowed to couple with the SPDP-labeled antigen or antibody, or SPDP-labeled peroxidase.

The present invention provides enhanced emissions using metallic structures of elliptical, spherical, triangular, rod-like forms or any geometric form. In exemplary cases, the elliptical islands have aspect ratios of 3/2, and the spherical colloids have diameters of 20-60 nm. Using known coating techniques, the placement of metallic structures could be controlled precisely, as close as 50 nm apart.

Further, the metallic structures can be fabricated to form a geometric shape such as triangle, square, oblong, elliptical, rectangle, or any shape that provides at least one apex area of the metallic surface. It is envisioned that the apex area includes not only pointed regions but regions with rounded edges such as found in an oblong or elliptical shape. The apex areas are preferably arranged so that one apex area is opposite from another apex area and aligned to cause the reactive zone to be positioned therebetween. The distances between the apex areas may range from 0.01 mm to 5 mm, more preferably from 2 mm to about 3 mm and depending on the size of the required reactive zone. The thickness of the metallic geometric shaped nanoburgers ranges from 25 nm to about 1000 nm, and more preferably from about 45 nm to about 250 nm.

The present invention further comprises a detection device for detecting emissions including, but not limited to visual inspection, digital (CCD) cameras, video cameras, photographic film, or the use of current instrumentation such as laser scanning devices, fluorometers, luminometers, photodiodes, quantum counters, plate readers, epifluorescence microscopes, fluorescence correlation spectroscopy, scanning microscopes, confocal microscopes, capillary electrophoresis detectors, or other light detector capable of detecting the presence, location, intensity, excitation and emission spectra, fluorescence polarization, fluorescence lifetime, and other physical properties of the fluorescent signal.

Excitation light sources can include arc lamps and lasers, natural sunlight, laser diodes and light emitting diode source, and both single and multiple photon excitation sources. In another embodiment, use of a Ti-sapphire laser, Laser Diode (LD) or Light Emitting Diode Sources (LEDs) may be used with the RNA assay of the present invention. For example, using 2-photon excitation at 700-1000 nm and also using short pulse width (<50 pi), high repetition rate (1-80 MHz), laser diode and LED (1 ns, 1-10 MHz) sources. The enhanced sensitivity of the assay using 2-photon excitation, as compared to 1-photon, can be shown by using series dilution with RNA, initially with the Ti-Sapphire system, and later with LEDs and LDs. If a fluorophore absorbs two photons simultaneously, it will absorb enough energy to be raised to an excited state. The fluorophore will then emit a single photon with a wavelength that depends on the fluorophore used and typically in the visible spectra. The use of the Ti-sapphire laser with infrared light has an added benefit, that being, longer wavelengths are scattered less, which is a benefit to high-resolution imaging. Importantly, there is reduced background signal level gained by using 2-photon excitation as compared to 1-photon excitation by utilizing localized excitation near by a metallic particles.

In one embodiment, the application of low level microwave heating of the sample may be used to speed up any chemical/biochemical kinetics within the system. Notably, low level microwaves do not destroy or denature proteins, DNA, or RNA, but instead heat the sample sufficiently to provide for accelerated kinetics such as binding or hybridization. In addition, the microwaves are not scattered by the metallic structures, which is contrary to most metal objects, such as that recognized by placing a spoon in a microwave oven.

Microwaves (about 0.3 to about 300 GHz) lie between the infrared and radiofrequency electromagnetic radiations. It is widely thought that microwaves accelerate chemical and biochemical reactions by the heating effect, where the heating essentially follows the principle of microwave dielectric loss. Polar molecules absorb microwave radiation through dipole rotations and hence are heated, where as non-polar molecules do not absorb due to lower dielectric constants are thus not heated. The polar molecules align themselves with the external applied field. In the conventional microwave oven cavity employed in this work, the radiation frequency (2450 MHz) changes sign $2.45 \times 10^9$ times per second. Heating occurs due to the tortional effect as the polar molecules rotate back and forth, continually realigning with the changing field, the molecular rotations being slower than the changing electric field. The dielectric constant, the ability of a molecule to be polarized by an electric field, indicates the capacity of the medium to be microwave heated. Thus, solvents such as water, methanol and dimethyl formamide are easily heated, where as microwaves are effectively transparent to hexane, toluene and diethylether. For metals, the attenuation of microwave radiation arises from the creation of currents resulting from charge carriers being displaced by the electric field. These conductance electrons are extremely mobile and unlike water molecules can be completely polarized in 10-18 s. In microwave cavity used in the present invention, the time required for the applied electric field to be reversed is far longer than this, in fact many orders of magnitude. If the metal particles are large, or form continuous strips, then large potential differences can result, which can produce dramatic discharges if they are large enough to break down the electric resistance of the medium separating the large metal particles. Interestingly, and most appropriate for the new assay platform described herein, small metal particles do not generate sufficiently large potential differences for this "arcing" phenomenon to occur. However, as discuss hereinbelow, the charge carriers which are displaced by the electric field are subject to resistance in the medium in which they travel due to collisions with the lattice phonons. This leads to Ohmic heating of the metallic structures in addition to the heating of any surface polar molecules. Intuitively, this leads to localized heating around the metallic structures in addition to the solvent, rapidly accelerating assay kinetics.

In the present invention, microwave radiation may be provided by an electromagnetic source having a frequency in a range between 0.3 and 10 GHz and a power level in a range between about 10 mwatts and 400 watts, more preferably from 30 mwatts to about 200 watts. Any source, known to one skilled in the art may be used, such as a laser that emits light, wherein light is used in its broad sense, meaning electromagnetic radiation which propagates through space and includes not only visible light, but also infrared, ultraviolet and microwave radiation. Thus, a single instrument placed above the surface of the assay can be used to generate the microwave energy and energy to excite fluorescing molecules. The light can be emitted from a fiber continuously or intermittently, as desired, to maintain the metallic particles at a predetermined temperature such that it is capable of increasing the speed of chemical reactions within the assay system. The microwave radiation may be emitted continuously or intermittently (pulsed), as desired. In the alternative, microwave energy can be supplied through a hollow wave guide for conveying microwave energy from a suitable magnetron. The microwave energy is preferably adjusted to cause an increase of heat within the metallic material without causing damage to any biological materials in the assay system.

Although fluorescence, chemiluminescence and/or bioluminescence detection has been successfully implemented, the sensitivity and specificity of these reactions require further improvements to facilitate early diagnosis of the prevalence of disease. In addition, most protein detection methodologies, most notably western blotting, are still not reliable methods for accurate quantification of low protein concentrations without investing in high-sensitivity detection schemes. Protein detection methodologies are also limited by antigen-antibody recognition steps that are generally kinetically very slow and require long incubation times; e.g., western blots require processing times in excess of 4 hours. Thus, both the rapidity and sensitivity of small-molecule assays are still critical issues to be addressed to improve assay detection. As such the use of low intensity ultrasound will increase the rapidity of the assay.

There are many important assays that can directly benefit from enhanced signal intensities and quicker kinetics. For example, myoglobin concentrations for heart attack patients, patients of toxic shock and pancreatitis. All of these assays are widely used in hospitals emergency rooms with assay times of greater than 30 minutes. Thus, the present invention can be used for points-of-care clinical assessment in emergency rooms.

Thus it would be advantages to increase speed of any chemical or biochemical reaction by using any device capable of generating and transmitting acoustic energy through any medium to transit ultrasonic atomizing energy. The ultrasonic emitting device can be placed in either the interior of a vessel used in a detection system or positioned adjacent thereto for transmitting energy into the vessel. The device may include components for the traditional electromagnetic stimulation of piezoelectric transducers, (man-made or naturally occurring), purely mechanical devices (such as high frequency air whistles or microphones), and laser devices. Individual components for acoustic energy systems are commercially available from a wide variety of manufacturers, which can be configured to particular applications and frequency ranges. (See Thomas Directory of American Manufacturers, Photonics Buyer's Guide, 1996, Microwave and RF, and Electronic Engineer's Master Catalogue).

Any oscillator or signal generator that produces a signal with predetermined characteristics such as frequency, mode, pulse duration, shape, and repetition rate may be used to generate acoustic frequencies for applying to the system of the present invention. Various oscillators or signal generators can be commercially purchased from a wide variety of manufacturers and in a variety of designs configured to particular applications and frequencies. Applicable transducers will include types that produce an acoustic wave within a range of frequencies (broadband) or for one specific frequency (narrowband) for frequencies ranging from hertz to gigahertz.

The acoustic delivery system will be variable depending on the application. For example, acoustic energy waves can be transmitted into liquid or solid source material either by direct contact of the source material with a transducer, or by coupling of transmission of the acoustic wave through another medium, which is itself in direct contact with the source material. If the source material is a liquid, a transducer can be placed in the liquid source material, or the walls of the vaporization vessel can be fabricated of a material that acts as a transducer thereby placing the liquid source material in direct contact with the transducer. Additionally, an acoustic energy emitting device may be positioned on the exterior of a system container for transmitting the appropriate energy. If the source material is a solid, a transducer can be placed in direct contact with it or the solid source material can be placed in a gas or liquid that is used as a coupling agent.

In the preferred acoustic frequencies any system that generates acoustic energy may be utilized. Preferably, the output of the ultrasonic generator is of a sufficient frequency to provide a movement flow within the system vessel to move molecules to the source of binding or reaction site without causing a large increase of heat in the system. For example, using the power output of 0.5 to 50 W at a frequency of 10 to 200 kHz, and more preferably from about 20 to 60 kHz and most preferably at about 40 kHz is effective.

To obtain the maximum transfer of acoustical energy from one medium to another, the characteristic acoustical impedance of each medium is preferably as nearly equal to the other as possible. The matching medium is sandwiched between the other two and should be the appropriate thickness relative to the wavelength of the sound transmitted, and its acoustical impedance R should be nearly equal to ($R_1$: $R_2$). Any impedance matching device that is commercially available can be utilized in the present invention.

The system may include ultrasonic vessels wherein at least a section of the vessel includes a transducer such as a piezoelectric transducer to generate acoustic vibrations. Such transducers can be located in the bottom of a vessel or in a plate whereon a vessel may be placed. Further such transducers can be placed at different levels on the vessel walls to enhance fluid flow within the vessel.

In the present invention, nanoburgers fabricated from metallic layered structures having hamburger type geometry show significantly enhanced fluorescence emission from fluorophores, when the fluorophores were positioned near the nanoburger structures of the present invention. In addition, a shorter fluorescence lifetime for fluorophores was observed and suggests that both an enhanced electric field and a plasmon-coupling component underpin the mechanism for fluorescence enhancement, near-to the SIFs-$SiO_2$-SIFs multilayered nanoburger structures.

EXAMPLES

Method and Materials

FITC (Fluorescein Isothiocyanate) was obtained from the Sigma-Aldrich Chemical company and used as received. Silane Prep™ glass microscope slides were purchased from Sigma-Aldrich.

Preparation of Nanoburger Substrates for Metal-Enhanced Fluorescence (MEF) Measurements The schematic of the SIFs nanoburger surface preparation is shown in FIG. 1. It includes three layers. The first layer is a silver film (SIF). SIFs were prepared as previously published.[39] In a typical SIFs preparation, a solution of silver nitrate (0.5 g in 60 ml of deionized water) was prepared in a clean 100-mL glass beaker. 200 µL of freshly prepared 5% (w/v) sodium hydroxide solution and 2 ml of ammonium were added to a continuously stirred silver nitrate solution at room temperature. Subsequently, the solution was cooled to 5° C. by placing the beaker in an ice bath, followed by soaking the Silane-Prep™ glass slides in the solution and adding a fresh solution of D-glucose (0.72 g in 15 ml of water). The temperature of the mixture was then allowed to warm to 30° C. As the color of the mixture turned from yellow green to yellowish brown, the slides were removed from the mixture, washed with water, and sonicated for 1 min at room temperature. The second layer consists of different thicknesses of $SiO_2$. The $SiO_2$ nanostructured films of various thicknesses were deposited onto SIFs slides using thermal vapor deposition, AccuCoat, Inc. Rochester, N.Y., USA. The third layer is again SIFs which were prepared using the same process as the first SIFs layer.

Preparation of the Sandwich Format Sample

A solution of 100 µL of a fluorophore (10 µM) was sandwiched between two glass slides for the control sample and between one glass and one nanoburger film (FIG. 3a) Fluorescein was excited with a continuous wave (CW) laser line at 455 nm and the fluorescence emission spectra measured as described below.

Fluorescence Lifetime Analysis

Fluorescence lifetimes were measured using the Time-Correlated Single Photon Counting technique, a Horiba Jobin Yvon fluorescence lifetime spectrometer (TemPro) with a 444 nm NanoLED as the light source. The intensity decays were analyzed in terms of the multi-exponential model:

$$I(t) = \sum_i \alpha_i \exp(-t/\tau_i) \quad (1)$$

Where $\alpha_i$ are the amplitudes and $T_i$ are the decay times, $$\sum_i \alpha_i = 1.0.$$

The fractional contribution of each component to the steady state intensity is given by $$f_i = \frac{\alpha_i \tau_i}{\sum_j \alpha_j \tau_j} \quad (2)$$

The mean lifetime of the excited state is given by $$\bar{\tau} = \sum_i f_i \tau_i \quad (3)$$

and the amplitude-weighted lifetime is given by $$\langle \tau \rangle = \sum_i \alpha_i \tau_i \quad (4)$$

The values of $\alpha_i$ and $\tau_i$ were determined by nonlinear least squares impulse reconvolution with a goodness-of-fit $X^2$ criterion.

Optical Spectroscopy

The extinction spectra of the nanostructured films of varying thicknesses were collected using a Varian Cary 50 UV-Vis spectrophotometer. Fluorescence spectra of the fluorophores was measured with blank glass sandwiches and glass-nanostructured film sandwiches using an Ocean Optics HD2000 fluorometer.

Atomic Force Microscopy (AFM)

AFM images were performed on a Molecular Imaging Picoplus Microscope. Samples were imaged at a scan rate of 1 Hz with 512×512 pixel resolution in a tapping mode. The surface roughness was measured using AFM. The surface roughness Sn is defined by the following expression:

$$S_n = \frac{1}{n}\sum_{i=1}^{n} |f(x_i, y_i) - \langle f_n \rangle| \quad (5)$$

Where $$\langle f_n \rangle = \frac{1}{n}\sum_{i=1}^{n} |f(x_i, y_i)| \quad (6)$$

is an average value of sampling f(xi,yi) and n is the sampling volume.

FDTD Calculations

The FDTD (Finite Difference Time Domain) method was employed here to determine the electric field intensities and distributions at the surface of two silver nanoparticles isolated by different thickness (1 nm-20 nm) $SiO_2$ in a Total Field Scattered Field (TFSF). TFSF sources are used to divide the computation area or volume into total field (incident plus scattered field) and scattered field only regions. The incident p-polarized electric field is defined as a plane wave with a wavevector that is normal to the injection surface. The scattered and total fields were monitored during the simulation such that the total or scattered transmission can be measured. Using Lumerical (Canada) FDTD Solution software, the simulation region was set to 600×600 nm with a mesh accuracy of 5. The overall simulation time was set to 50 fsec and calculated over a wavelength range from 300-800 nm.

Results and Discussion

Figure 2:
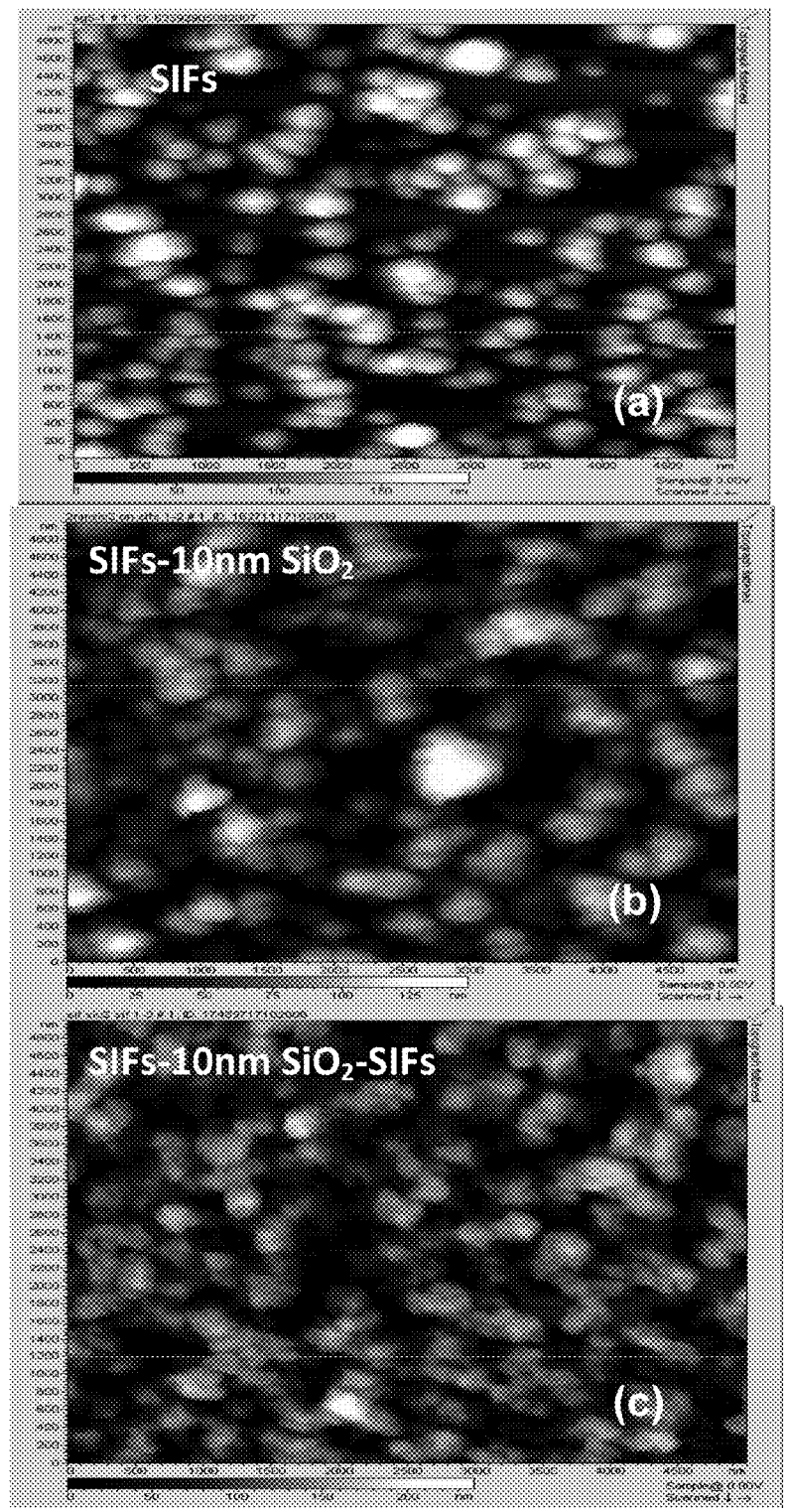
FIG. 2 shows AFM images of SIFs (a), SIFs-10 nm $SiO_2$ (b), and nanoburger (SIFs-10 nm $SiO_2$-SIFs) (c). The respective line scans of the AFM images are shown in (d) (e) and (f). Roughness=32.5 nm for SIFs, roughness=25.7 nm for SIFs-10 nm $SiO_2$, roughness=37.9 nm for SIFs-10 nm $SiO_2$-SIFs.
Figure 2:
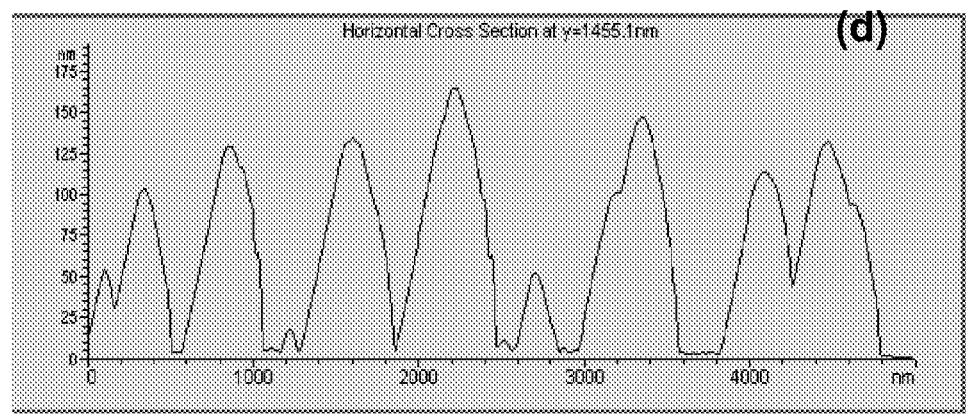
Figure 2:
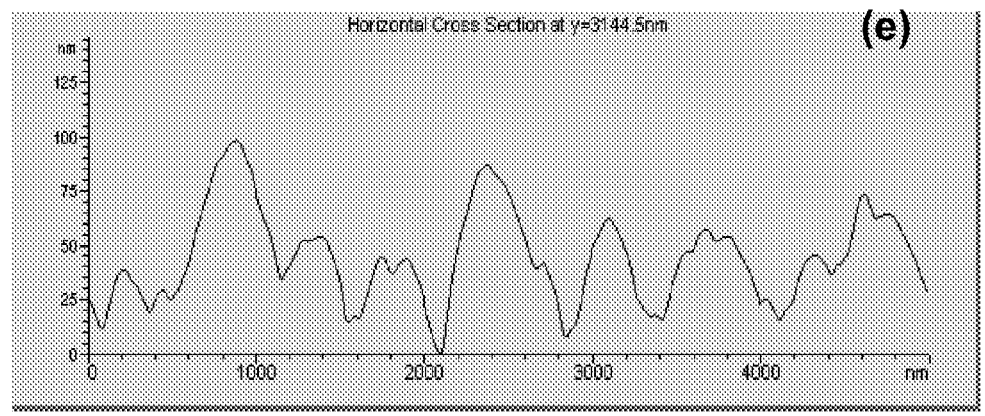
Figure 2:
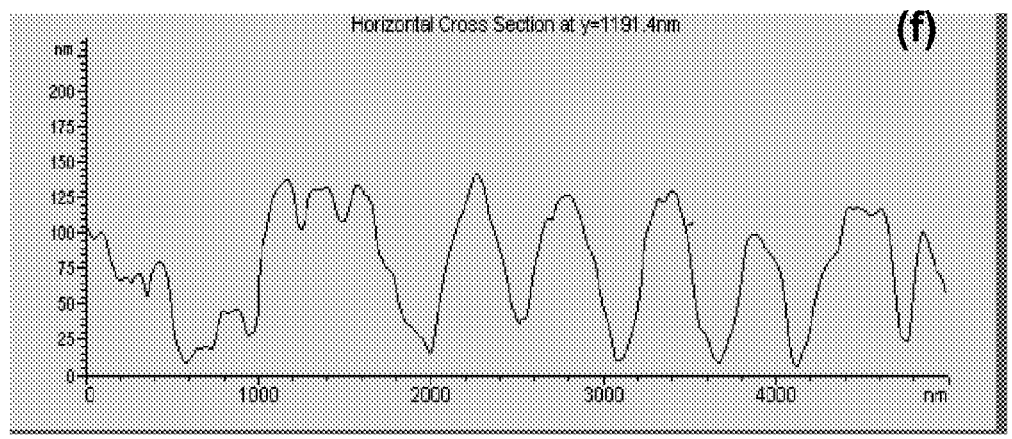

The morphology of a series of SIFs nanoburger structures were firstly studied using AFM. FIG. 2 shows the morphology of SIFs, SIFs/10 nm $SiO_2$ and SIFs/10 nm $SiO_2$/SIFs. It can be seen, for the first layer of the SIFs films (FIG. 2a), an irregular size of 125 nm Ag particles with a surface roughness around 32.5 nm can be observed. After deposition of $SiO_2$ (FIG. 2b), it can be seen that the film surface is much smoother with a roughness around 25.7 nm, due to the deposition of the $SiO_2$. When the second layer of SIFs was deposited onto the $SiO_2$ (FIG. 2c), a fairly unstructured silver film with roughness around 37.9 nm and a particle size around 125 nm was observed.

Figure 3:
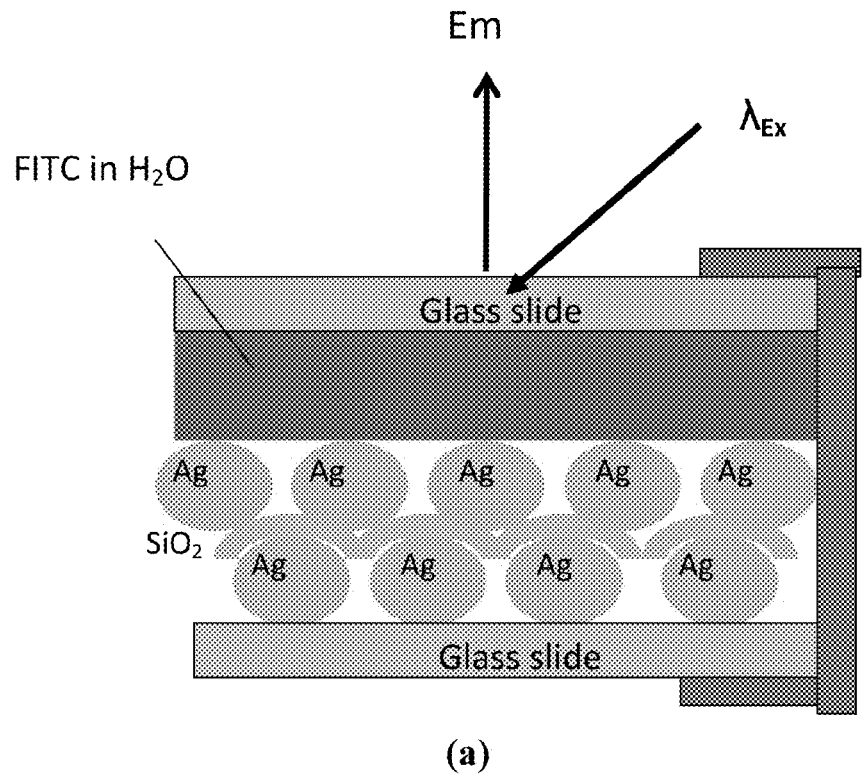
FIG. 3 shows a geometry schematic for FITC solutions sandwiched between one glass and a nanoburger slide (a). Absorbance spectra of SIFs-5 nm $SiO_2$ and SIFs-5 nm $SiO_2$-SIFs (b). Absorbance spectra of FITC on SIFs-5 nm $SiO_2$ and on $SIO_2$-5 nm $SiO_2$-SIFs (c). Absorbance spectra of FITC solution measured in a cuvette (d).
Figure 3:
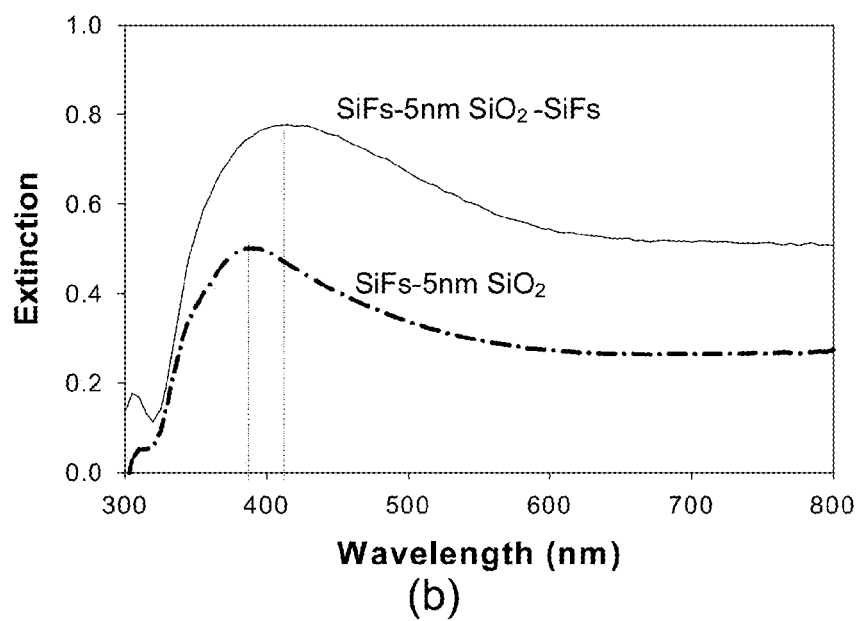
Figure 3:
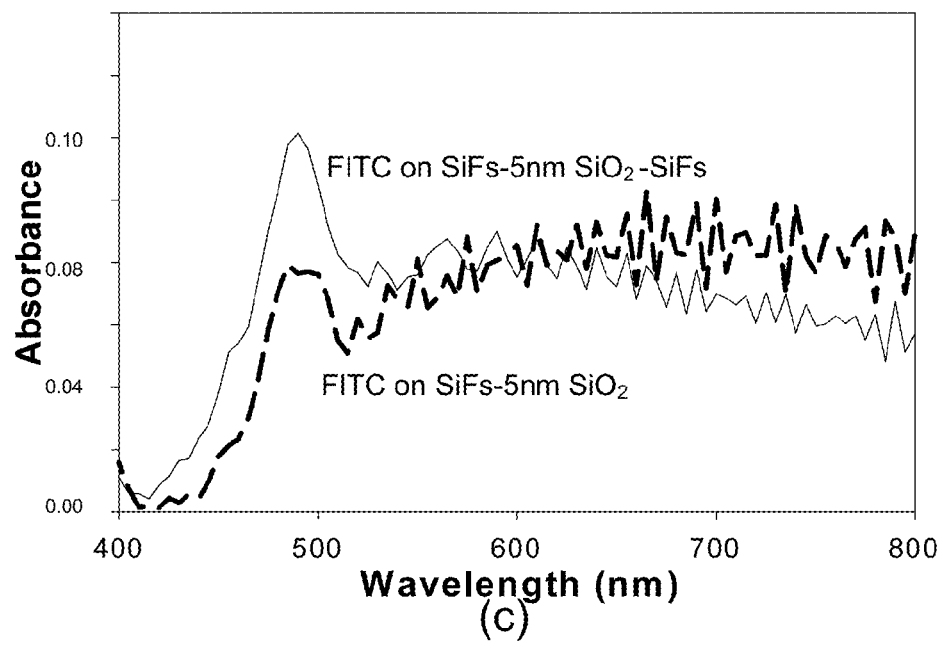
Figure 3:
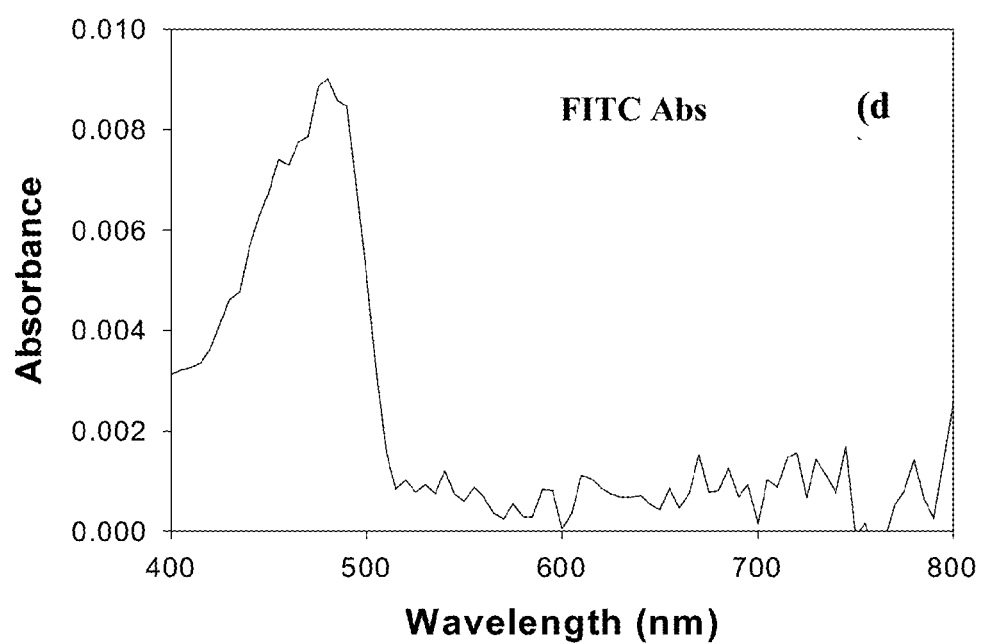

FIG. 3b shows the extinction spectra of SIFs nanoburger structure "SIFs-5 nm $SiO_2$-SIFs" and compared to SIFs-5 nm $SiO_2$. It can be seen that the SIFs nanoburger structure has a much larger extinction spectra with maximum wavelength red shifted (410 nm) as compared to a single layer of SIFs/5 nm $SiO_2$ (390 nm). This increase in extinction is attributed to the higher cumulative optical density of two layers of SIFs compared with one layer SIFs and the subsequent wavelength shift is attributed to the near-field refractive index change between individual SIFs with the $SiO_2$ isolation layer. The absorption of Fluorescein on SIFs nanoburger structure "SIFs-5 nm $SiO_2$-SIFs" and compared to SIFs-5 nm $SiO_2$ is shown in FIG. 3c using SIFs-5-nm $SiO_2$ and SIFs-5 nm $SiO_2$-SIFs films as background respectively. It can be seen that the Fluorescence has a much larger absorbance on "SIFs-5 nm $SiO_2$-SIFs" as compared to that on SIFs-5 nm $SiO_2$ alone, which has the same maximum absorbance wavelength of FITC (FIG. 3 d).

For nanoburger structures with different thickness of $SiO_2$, similar extinction was observed, where there was much large extinction spectra as compared to a single layer of SIFs/x nm $SiO_2$. These effects can be explained as a result of the coupling of the molecular dipoles with the localized electromagnetic field of the metallic particle's surface plasmon resonance (Localized Plasmon Resonance, LPR) in the ground state. In essence, conducting metallic particles can modify the free-space far-field absorption condition (observed in the absence of metal) in ways that increase the incident electric field, Em, felt by close-proximity near-field fluorophores.[37]

Figure 4:
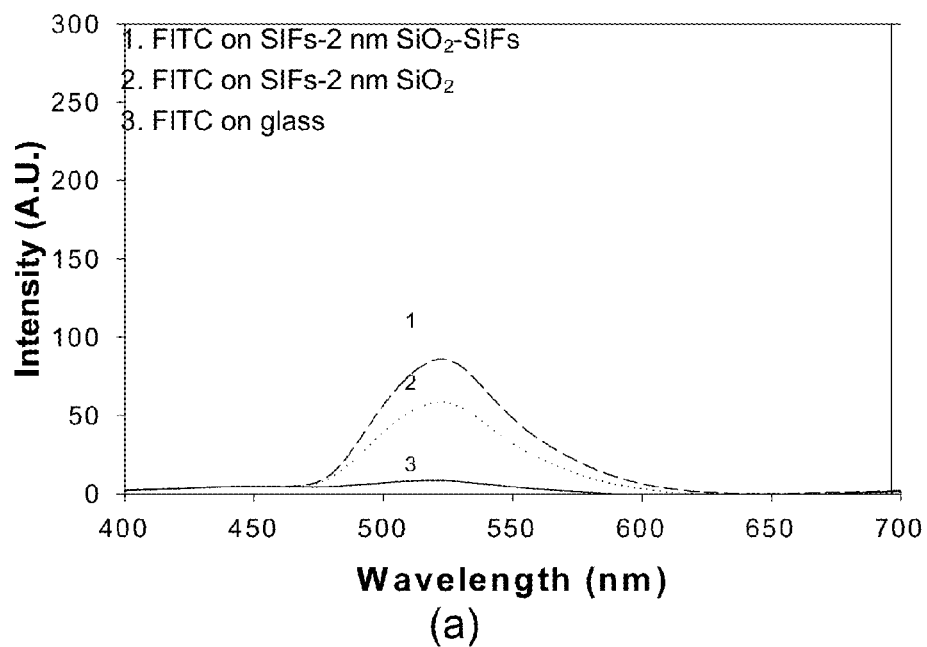
FIG. 4 shows the fluorescence spectra and enhancement factor of FITC solutions sandwiched between one glass and nanoburger slides with different $SiO_2$ thicknesses. (a:2 nm $SiO_2$, b:5 nm $SiO_2$, c:7 nm $SiO_2$, d:10 nm $SiO_2$, e:15 nm $SiO_2$). Excitation: 455 nm.
Figure 4:
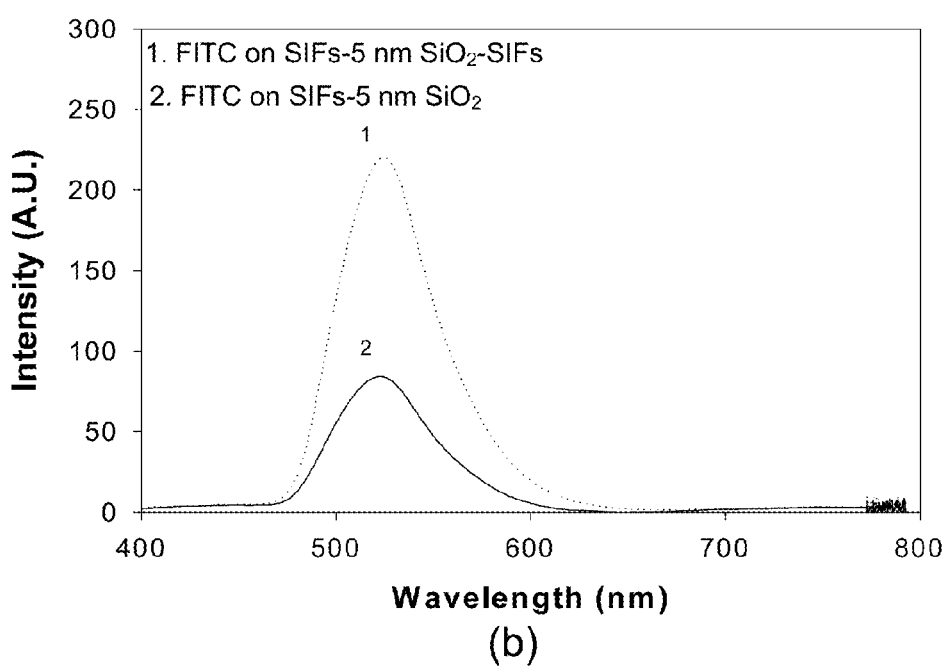
Figure 4:
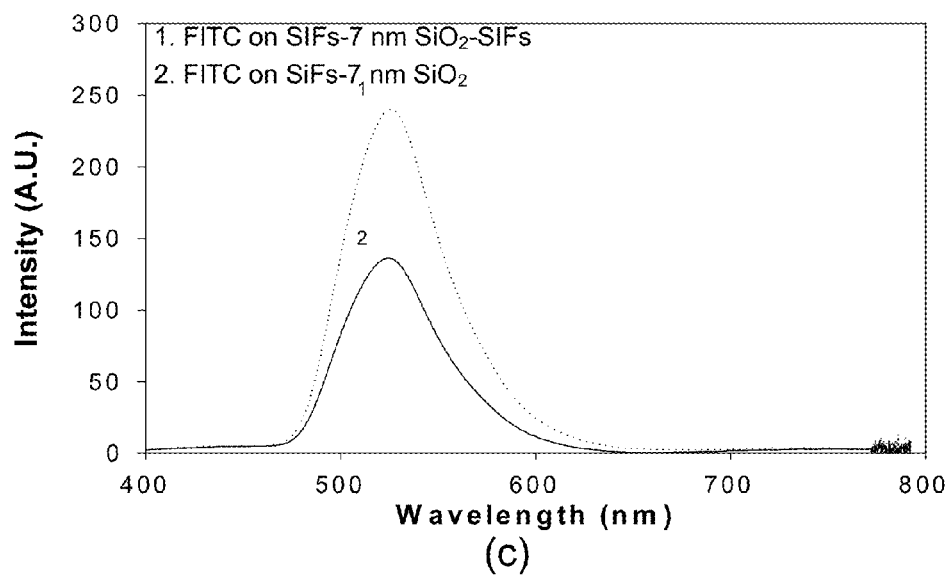
Figure 4:
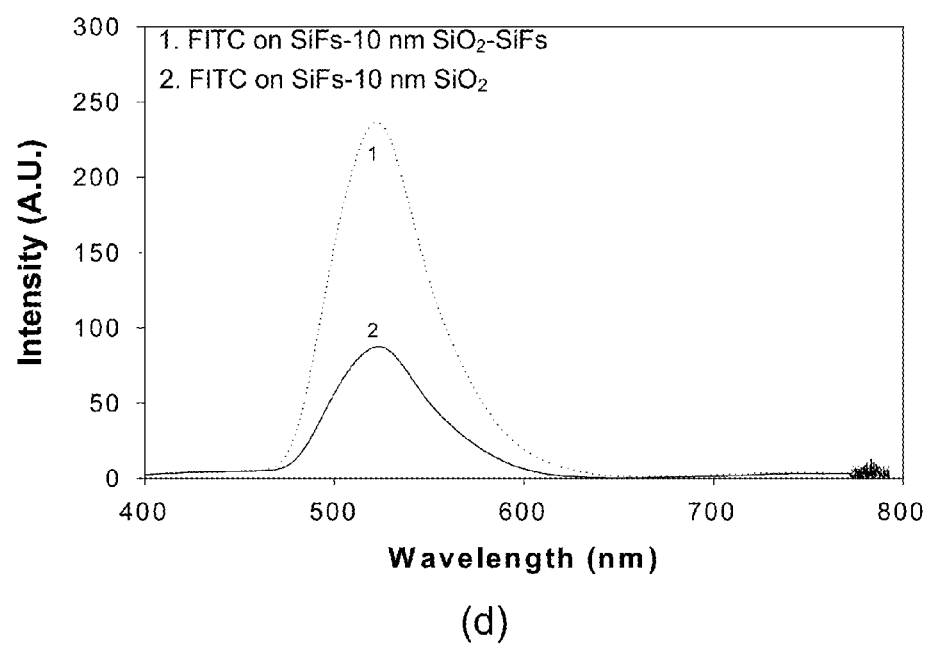
Figure 4:
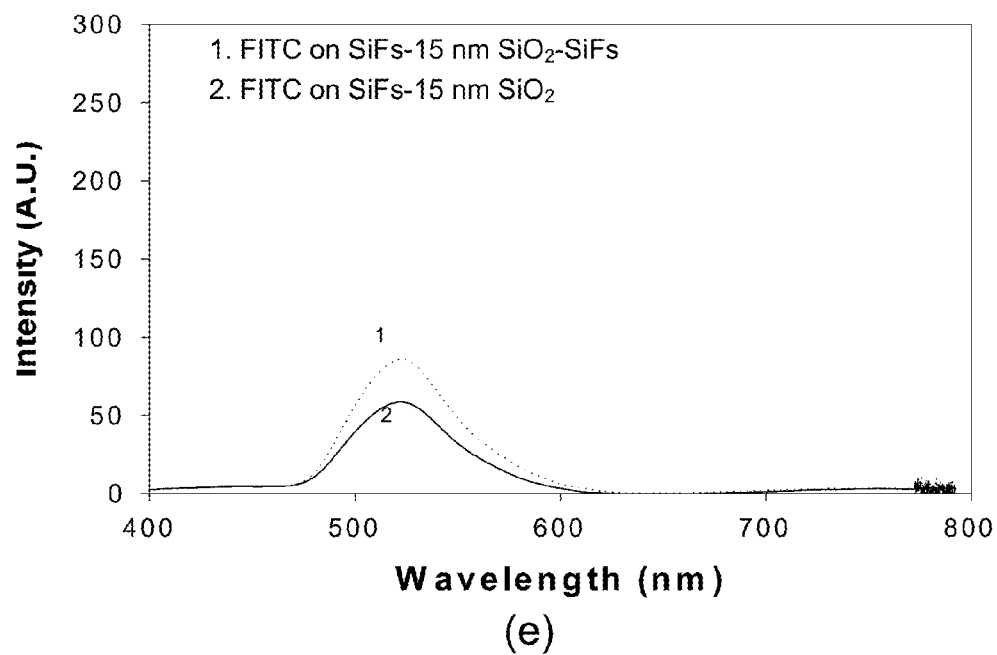
Figure 4:
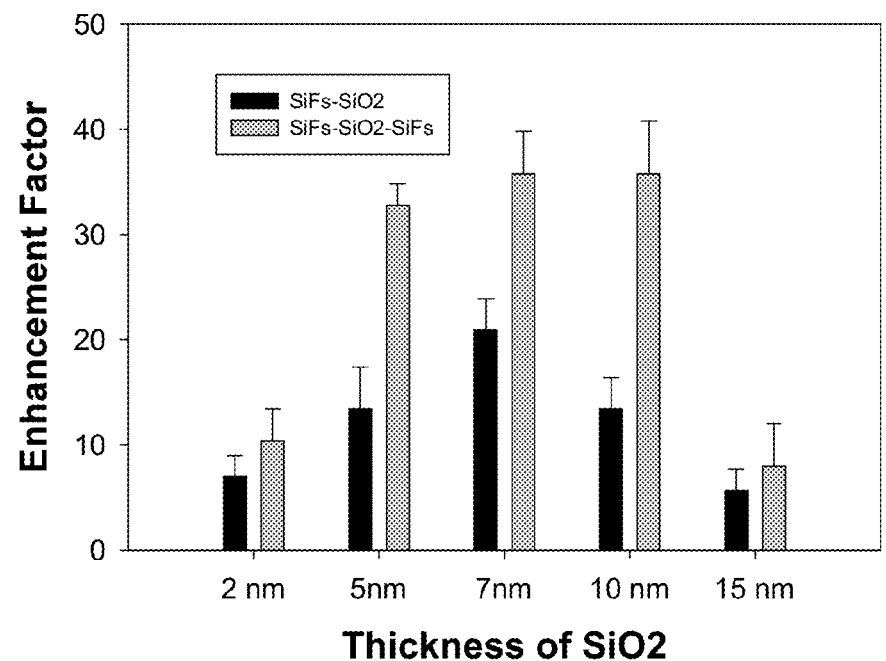

To test the nanoburger substrate for better potential applications in MEF, the fluorescence emission spectra of Fluorescein in water on SIFs-$SiO_2$-SIFs films with different thickness of $SiO_2$, and on glass were measured with excitation 455 nm with the spectra and enhancement factor compiled in FIG. 4. From FIG. 4(f), it can be seen that the fluorescence of Fluorescein is enhanced (≈35 times) for SIFs-7 nm $SiO_2$-SIFs and SIFs-10 nm $SiO_2$-SIFs, where the enhancement factor increased with increased SIFs-7 nm $SiO_2$ thickness is 20 times and 14 times for SIFs-10 nm $SiO_2$-SIFs. Also it was observed that the fluorescence enhancement factor (as compared to a plain glass control sample) was increased with the $SiO_2$ thickness increase (from 2 nm to 10 nm) and dropped when the $SiO_2$ thickness reached about 15 nm. Also, the fluorescence enhancement factor from the nanoburger substrate is much larger than that of one single layer of SIFs without $SiO_2$,[14, 35, 36, 38] where the enhanced emission are facilitated by the close proximity of the fluorophore to the nanoburger layers, i.e. a near-field interaction. Thus, this enhancement effect loosely correlates with an enhanced electric field component from the substrates, as simulated using FDTD, suggesting that an enhanced absorption contributes significantly to MEF.

Figure 5:
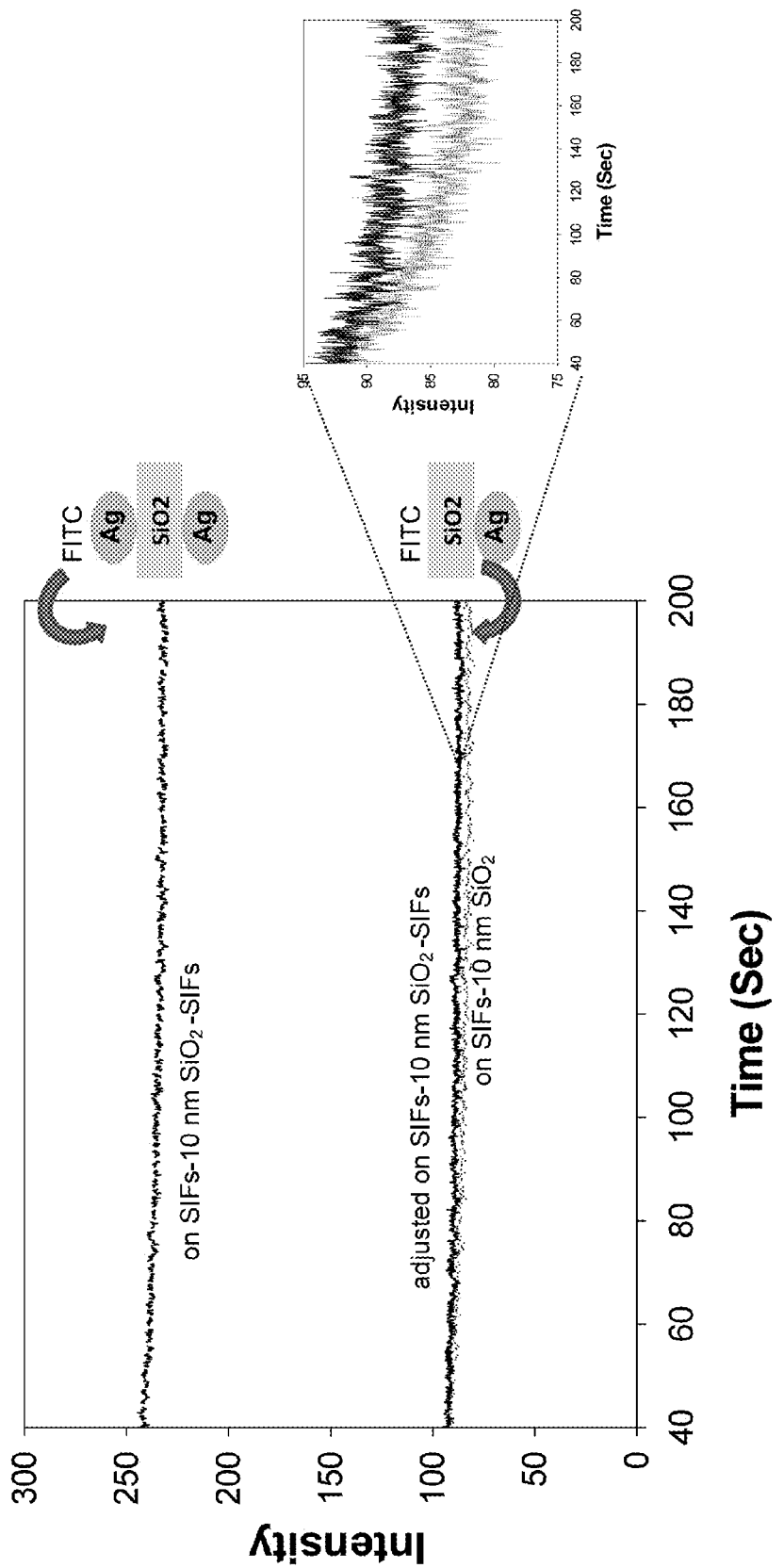
FIG. 5 shows the emission intensity vs. time of FITC on SIFs-10 nm $SiO_2$ and SIFs-10 nm-$SiO_2$-SIFs and with the laser power adjusted to give the same initial steady state fluorescence intensity as observed on SIFs-10 nm $SiO_2$, (bottom curves).

The photostability (steady-state intensity decay) of fluorescence on SIFs-10 nm $SiO_2$ and SIFs-10 nm $SiO_2$-SIFs was also measured. FIG. 5 shows fluorescence emission as a function of time, excited at 455 nm and observed through a 500 nm long pass filter. The relative intensities of the plots reflect that more detectable photons can be observed per unit time from the Ws-10 nm $SiO_2$-SIFs film, as compared to SIFs-$SiO_2$, where the integrated areas under the plots is proportional to the photon flux from the respective surfaces.

By additionally adjusting the laser power to match the same initial steady-state intensities of the samples at time t=0, the FITC on SIFs-10 nm $SiO_2$-SIFs can be seen to be more photostable (FIG. 5). Similar findings were observed for the other SIFs-$SiO_2$ geometries studied. This finding of enhanced photostability subsequently implies that the lifetime of the SIFs-10 nm $SiO_2$-SIFs is shorter than on the SIFs-10 nm $SiO_2$ film, the fluorophore in essence spending less time on average in an excited state due to the fast non-radiative energy transfer to the SIFs-10 nm $SiO_2$-SIFs, and therefore is less prone to photo destruction, i.e. is more photostable. In terms of a substrate for analytical chemistry applications, then a higher photon flux (counts per unit time) will invariably increase the fluorescence detectability from the surfaces.

The time-resolved intensity decays of fluorescein (fluorescence lifetimes) was measured in close proximity to SIFs and nanoburger structures, data shown in Table 1, using the time-correlated single photon counting technique.

TABLE 1

Fluorescence lifetime analysis of FITC in water and on SIFs nanoburger deposits measured using time-domain Fluorometry.

|  | T1 ns | A1 % | T2 ns | A2 % | <τ> ns | τ ns | $\chi^2$ |
|---|---|---|---|---|---|---|---|
| FITC/glass | 4.44 | 95.37 | 10.27 | 4.63 | 4.71 | 5.02 | 1.05 |
| FITC/SIFs | 4.02 | 92.37 | 8.27 | 7.63 | 4.34 | 4.63 | 1.05 |
| FITC/SIFs-7 nm $SiO_2$ | 2.61 | 91.25 | 10.4 | 8.75 | 3.29 | 4.76 | 1.02 |
| FITC/SIFs-7 nm $SiO_2$ -SIFs | 1.94 | 95.33 | 7.77 | 4.67 | 2.21 | 2.89 | 0.92 |
| FITC/SIFs-10 nm $SiO_2$ | 2.60 | 90.25 | 10.1 | 9.75 | 3.30 | 4.68 | 1.04 |
| FITC/SIFs-10 nm $SiO_2$ -SIFs | 1.91 | 94.53 | 7.71 | 5.47 | 2.21 | 3.00 | 0.95 |

τ mean lifetime, <τ>-amplitude-weighted lifetime.

The respective lifetimes were calculated from those decays, using non-linear least squares impulse reconvolution analysis. Both a reduced amplitude lifetime (<τ> on SIFs-7 nm $SiO_2$ and SIFs-7 nm $SiO_2$-SIFs is 3.29 ns and 2.21 ns respectively) and mean lifetime ($\tau_{mean}$ on SIFs-7 nm $SiO_2$ and SIFs-7 nm $SiO_2$-SIFs is 4.76 ns and 2.89 ns, (<τ> on SIFs-10 nm $SiO_2$ and SIFs-10 nm $SiO_2$-SIFs is 3.30 ns and 2.21 ns respectively) and mean lifetime ($\tau_{mean}$ on SIFs-10 nm $SiO_2$ and SIFs-10 nm $SiO_2$-SIFs is 4.68 ns and 3.0 ns) was observed as compared to the glass control sample ($\tau_{mean}$ on glass=5.02 ns and <τ> on glass=4.71 ns). These findings of reduced fluorophore lifetimes are consistent with previously reported findings for nanosecond decay time fluorophores sandwiched between single layer silver nanostructures but having no $SiO_2$ component which suggest the radiating plasmon model[39-41] is a suitable description of the nanoburger fluorescence enhancement mechanism. Notably, the lifetime of the fluorophore-metal system is reduced due to a faster and more efficient fluorophore-plasmon coupling, followed in turn by coupled-system emission, the plasmon in essence radiating the coupled quanta through the scattering component of its extinction spectrum.

Figure 6:
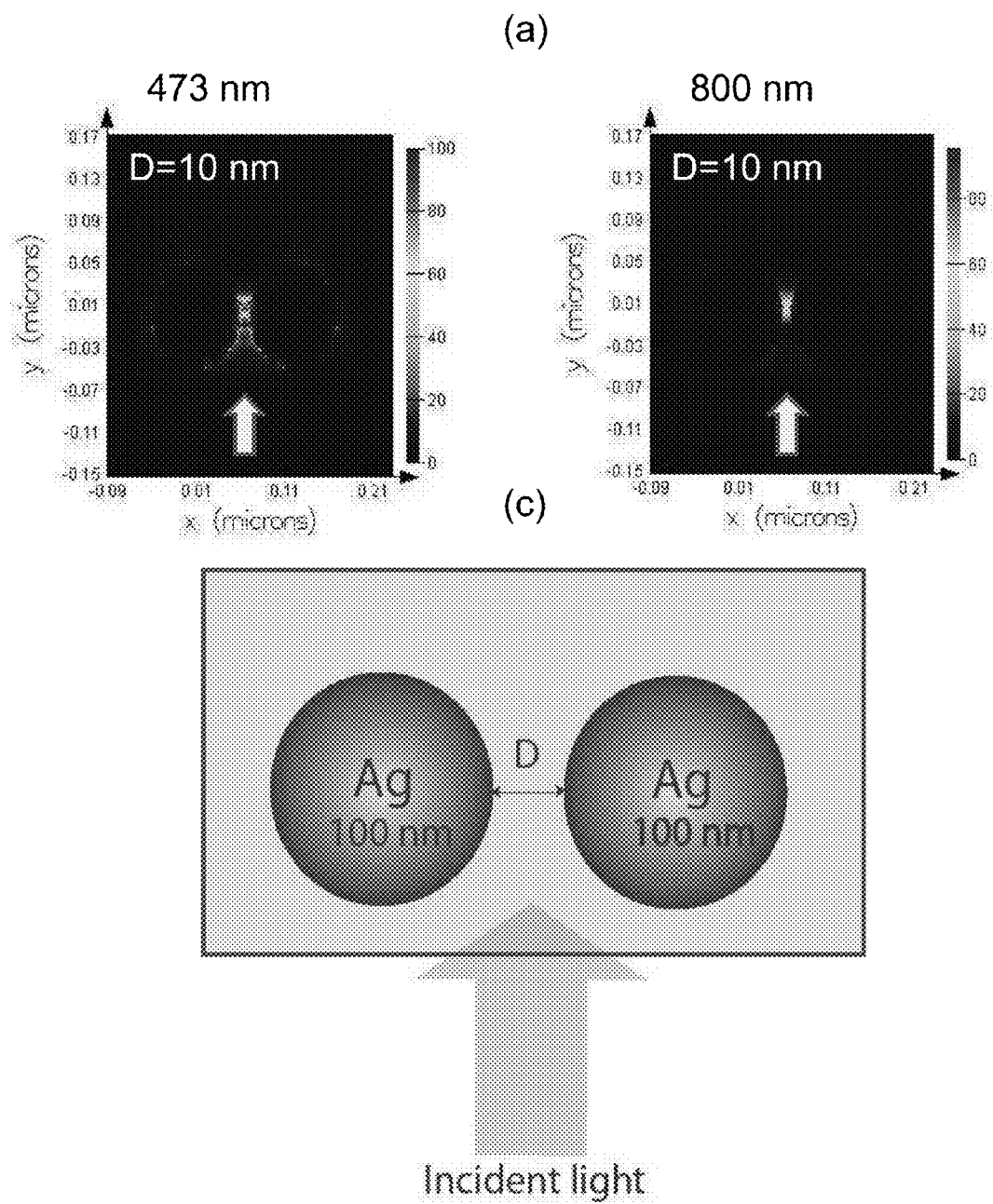
FIG. 6 shows dependences of the E-field intensity upon the distance (D=10 nm) between NPs for two wavelengths of the incident light: 473 nm and 800 nm(a). The images of the 2D E-field distribution around silver NPs for incident light wavelengths of 473 nm and 800 nm (arrows show the direction of the incident light). The $|Ex^2+Ey^2|_{max}$ was cal- culated along the D-axis (b) which is perpendicular to the direction of the applied incident far-field. Cartoon shows the set up for the FDTD calculations of the near-field intensity that were made for 100 nm diameter silver NPs, background refractive index of 1.5 ($SiO_2$) (c).
Figure 6:
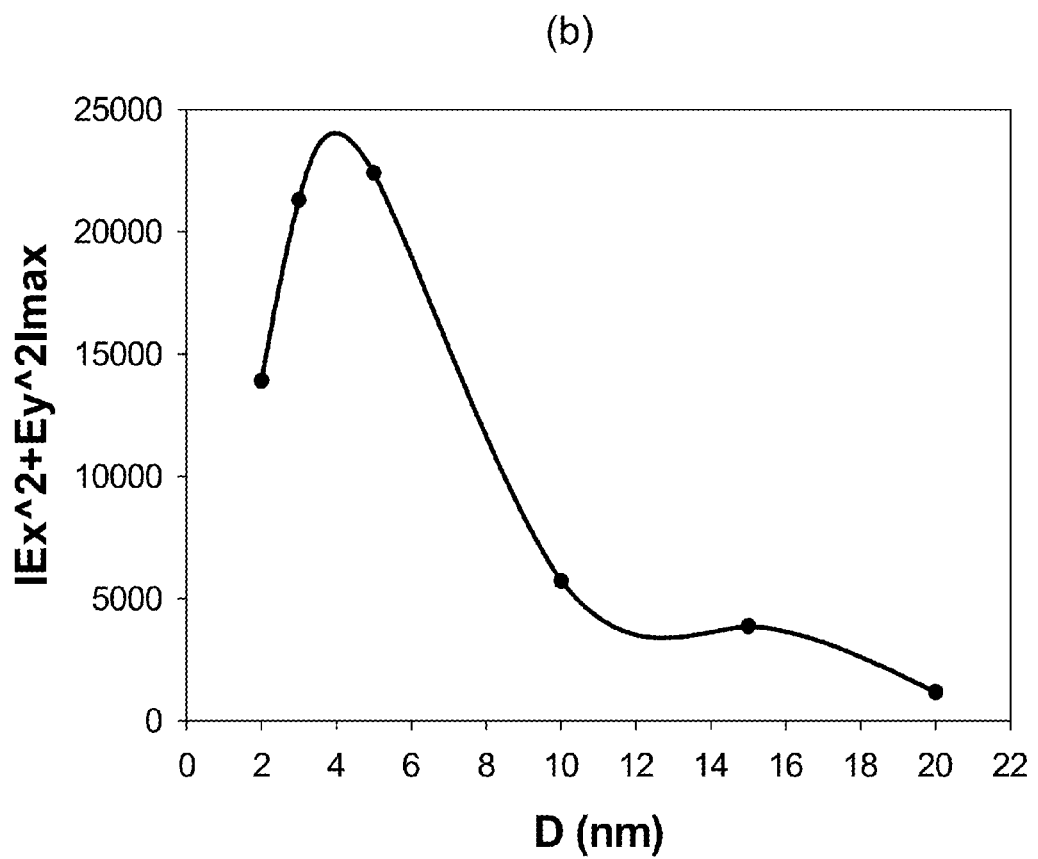

It is proposed that there are two complementary effects for the observed fluorescence enhancement caused by the metallic nanoburger of the present invention including: i) surface plasmons can radiate coupled fluorescence efficiently, and ii) an enhanced absorption or electric field facilitates enhanced emission. Since enhanced electromagnetic fields in proximity to metal nanoparticles is the basis for the increased system absorption in MEF, the electric field distributions for nanoburger nanostructures with various $SiO_2$ thickness was calculated using FDTD calculations (FIG. 6). FDTD calculations show that the maximum electric field of the nanoburger structure increases with the thickness of $SiO_2$ increasing and then decreases when thickness of $SiO_2$ exceeds 15 nm similar to that observed experimentally i.e. FIG. 4.[42] However, the values are not identical, which is simply explained by the differences between empirical and theoretical data.

It is proposed that there are two theories for mechanisms of the results shown herein including enhanced absorption and a reduced lifetime. Notably, as shown herein a fluorophore near-to the SIFs nanoburger structures can display an enhanced absorption, shown experimentally in FIG. 3, which has been further modeled in FIG. 6, with a modest correlation between both sets of data. In this regard, an enhanced absorption of the fluorophore does not lend itself to a reduced fluorescence lifetime which is related to the plasmon coupling component.[39]

For fluorophores in the far-field condition (i.e. greater than 1 wavelength away from the nanoburger structures), the fluorescence quantum yield and lifetime are described by the classical equations:

$$Q_0 = \frac{\Gamma}{\Gamma + k_{nr}} \quad (7)$$

$$\tau_0 = \frac{1}{\Gamma + k_{nr}} \quad (8)$$

Where $\Gamma$ is the far-field fluorophore radiative rate. Knr, are the none-radiative rates, $Q_0$ the quantum yield and $\tau_o$ is the free space lifetime. From these two equations, it can be seen that as one modifies the Knr rates, such as by adding a quencher, both the quantum yield and lifetime change in unison.

However, for fluorescein solutions close-to the nanoburger structures it was noted that there was both an enhanced emission, $Q_m$ and this was coupled with a reduced lifetime, $\tau_m$, which is quite different than the traditional free space condition, i.e. equations 7 and 8, shown above. Such equations are modified and such modification are shown in equations 9 and 10, where $\tau_m$, $Q_m$ and $\Gamma_m$ are the metal-modified system lifetimes, quantum yields (overall brightness) and system radiative rates respectively.

$$Q_m = \frac{\Gamma + \Gamma_m}{\Gamma + \Gamma_m + k_{nr}} \quad (9)$$

$$\tau_m = \frac{1}{\Gamma + \Gamma_m + k_{nr}} \quad (10)$$

From FIG. 5, it is noted that a better fluorescein photostability is exhibited which is attributed to the reduced fluorophore lifetime near-to metal (confirmed by time-resolved measurements, Table I), the fluorophore spending on average less time in an excited state prior to its deactivation to the ground state, and thus has less time for photochemical excited state reactions, i.e. is more photostable. The presence of both an enhanced absorption and a reduced lifetime, suggests two complimentary mechanisms for fluorescence enhancement.

Thus, the first observation of MEF from the layers of SIFs/$SiO_2$/SIFs, referred to as nanoburger substrates, due to the similarity to a hamburger-type geometry, showed significantly enhanced fluorescence intensity, decreased lifetimes and an increased photostability, when fluorophores were placed in close-proximity to the multilayer nanoburger structure as compared to single layered SIFs, which hither to, have been the most widely used substrate in MEF studies. Furthermore, the enhancement factor can be tuned by changing the $SiO_2$ thickness between the SIFs layers, a result for the changing e-field between the particles.

REFERENCES

The contents of all references cited herein are hereby incorporated by reference herein for all purposes.
1. Alfano, R. R.; Tang, G. C.; Pradhan, A.; Lam, W.; Choy, D. S. J.; Opher, E., Fluorescence-Spectra from Cancerous and Normal Human-Breast and Lung Tissues. *Ieee Journal of Quantum Electronics* 1987, 23, (10), 1806-1811.
2. Chance, R. R.; Miller, A. H.; Prock, A.; Silbey, R., Fluorescence and Energy-Transfer near Interfaces—Complete and Quantitative Description of Eu+3-Mirror Systems. *Journal of Chemical Physics* 1975, 63, (4), 1589-1595.
3. Choi, S.; Choi, E. Y.; Kim, D. J.; Kim, J. H.; Kim, T. S.; Oh, S. W., A rapid, simple measurement of human albumin in whole blood using a fluorescence immunoassay (I). *Clin Chim Acta* 2004, 339, (1-2), 147-56.
4. Cullum, M. E.; Lininger, L. A.; Schade, S. Z.; Cope, S. E.; Ragain, J. C., Jr.; Simonson, L. G., Diagnosis of militarily relevant diseases using oral fluid and saliva antibodies: fluorescence polarization immunoassay. *Mil Med* 2003, 168, (11), 915-21.
5. Davidson, R. S.; Hilchenbach, M. M., The Use of Fluorescent-Probes in Immunochemistry. *Photochemistry and Photobiology* 1990, 52, (2), 431-438.
6. Andersson, H.; Baechi, T.; Hoechl, M.; Richter, C., Autofluorescence of living cells. *Journal of Microscopy-Oxford* 1998, 191, 1-7.
7. Enderlein, J.; Ruckstuhl, T.; Seeger, S., Highly efficient optical detection of surface-generated fluorescence. *Applied Optics* 1999, 38, (4), 724-732.
8. Thompson, R. B., *Fluorescence Sensors and Biosensors.* CRC Press, Taylor & Francis Group, LLC: Boca Raton Fla., 2006.
9. Chowdchury, S.; Bhethanabotla, V.; sen, R., Silver-copper alloy nanoparticles for metal enhanced luminescence. *Applied Physics Letters* 2009, 95, (13), 1311-15.
10. Stefani, F.; Vasilev, K.; Bocchio, N.; Stoyanova, N.; Kreiter, M., Surface-plasmon-mediated single-molecule fluorescence through a thin metallic film. *Physical Review Letters* 2005, 94, (2).
11. Garrett, S.; Smith, L.; Barnes, W., Fluorescence in the presence of metallic hole arrays. *Journal of Modern Optics* 2005, 52, (8), 1105.
12. Praharaj, S.; Ghosh, S.; Nath, S.; Kundu, S.; Panigrahi, S.; Basu, S.; Pal, T., Size-selective synthesis and stabilization of gold organosol in CnTAC:Enhanced molecular fluorescence from gold-bound fluorophores. *Journal of physical CHEMISTRY B* 2005, 109, (27), 13166.
13. Stranik, O.; McEvoy, H.; McDonagh, C.; MacCraith, B., Plasmonic enhancement of fluorescence for sensor applications. *Sensors and Actuators B—Chemical* 2005, 107, (1), 148.
14. Aroca, R.; Kovacs, G. J.; Jennings, C. A.; Loutfy, R. O.; Vincett, P. S., Fluorescence Enhancement from Langmuir-Blodgett Monolayers on Silver Island Films. *Langmuir* 1988, 4, (3), 518-521.
15. Chen, Y.; Munechika, K.; Ginger, D. S., Dependence of fluorescence intensity on the spectral overlap between 16. Cheng, P. P.; Silvester, D.; Wang, G.; Kalyuzhny, G.; Douglas, A.; Murray, R. W., Dynamic and static quenching of fluorescence by 1-4 nm diameter gold monolayer-protected clusters. *J Phys Chem B Condens Matter Mater Surf Interfaces Biophys* 2006, 110, (10), 4637-44.
17. Croce, A. C.; Ferrigno, A.; Vairetti, M.; Bertone, R.; Freitas, I.; Bottiroli, G., Autofluorescence properties of isolated rat hepatocytes under different metabolic conditions. *Photochemical & Photobiological Sciences* 2004, 3, (10), 920-926.
18. Doron, A.; Katz, E.; Willner, I., Organization of Au Colloids as Monolayer Films onto Ito Glass Surfaces—Application of the Metal Colloid Films as Base Interfaces to Construct Redox-Active Monolayers. *Langmuir* 1995, 11, (4), 1313-1317.
19. Kawasaki, M.; Mine, S., Enhanced molecular fluorescence near thick Ag island film of large pseudotabular nanoparticles. *Journal of Physical Chemistry B* 2005, 109, (36), 17254-17261.
20. Malicka, J.; Gryczynski, I.; Geddes, C. D.; Lakowicz, J. R., Metal-enhanced emission from indocyanine green: a new approach to in vivo imaging. *J Biomed Opt* 2003, 8, (3), 472-8.
21. Dostalek, J.; knoll, W., Biosensors based on surface plasmon-enhanced fluorescence spectroscopy. *Biointerphases* 2008, 3, (3), FD12.
22. Gersten, J. I., *Theory of fluorophore-metallic surface interactions*. Springer: New York, 2004; Vol. 8, p 197-221.
23. Kasry, A.; Knoll, W., Long range surface plasmon fluorescence spectroscopy. *Applied Physics Letters* 2006, 89, (10), 101106.
24. Geddes, C. D.; Lakowicz, J. R., Metal-enhanced fluorescence. *Journal of Fluorescence* 2002, 12, (2), 121-129.
25. Aslan, K.; Malyn, S. N.; Geddes, C. D., Angular-dependent metal-enhanced fluorescence from silver colloid-deposited films: opportunity for angular-ratiometric surface assays. *Analyst* 2007, 132, (11), 1112-1121.
26. Aslan, K.; Lakowicz, J. R.; Szmacinski, H.; Geddes, C. D., Metal-enhanced fluorescence solution-based sensing platform. *Journal of Fluorescence* 2004, 14, (6), 677-679.
27. Aslan, K.; Malyn, S. N.; Geddes, C. D., Metal-enhanced fluorescence from gold surfaces: angular dependent emission. J Fluoresc 2007, 17, (1), 7-13.
28. Zhang, Y.; Aslan, K.; Previte, M. J. R.; Geddes, C. D., Metal-enhanced fluorescence from copper substrates. *Applied Physical Letters* 2007, 90, (17), 173116.
29. Aslan, K.; Previte, M. J. R.; Zhang, Y.; Geddes, C. D., Metal-Enhanced Fluorescence from Nanoparticulate Zinc Films. *Journal of Physical Chemistry C.* 2008, 112, (47), 18368-18375.
30. Pribik, R.; Aslan, K.; Zhang, Y.; Geddes, C. D., Metal-Enhanced Fluorescence from Chromium Nanodeposits. *Journal of Physical Chemistry C.*, 2008, 112, 17969-17973.
31. Zhang, Y.; Dragan, A.; Geddes, C. D., Near-Infrared Metal-Enhanced Fluorescence Using Nickel Nanodeposits. submitted to *Journal of Physical Chemistry C* 2009.
32. Zhang, Y.; Dragan, A.; Geddes, C. D., Metal-Enhanced Fluorescence from Tin nanostructured Surfaces *Accepted by Journal of Applied Physics* 2009.
33. Zhang, Y.; Padhyay, A.; Sevilleja, J. E.; Guerrant, R. L.; Geddes, C. D., Interactions of the Fluorophores with Iron Nanoparticles: Metal—Enhanced Fluorescence submitted to the *Journal of Physical Chemistry C* 2010.
34. Aslan, K.; Badugu, R.; Lakowics, J. R., Metal-enhanced fluorescence from plastic substrate. *Journal of Fluorescence* 2005, 15, (2), 99.
35. Garoff, S.; Weitz, D. A.; Gramila, T. J.; Hanson, C. D., Optical-Absorption Resonances of Dye-Coated Silver-Island Films. *Optics Letters* 1981, 6, (5), 245-247.
36. Zhang, Y.; Dragan, A.; Geddes, C. D., Wavelength—Dependence of Metal-Enhanced Fluorescence. *Journal of Physical Chemistry C.* 2009, 113 12095-12100.
37. Lakowicz, J. R., Radiative decay engineering: Biophysical and biomedical applications. *Analytical Biochemistry* 2001, 298, (1), 1-24.
38. Aslan, K.; Badugu, R.; Lakowicz, J. R.; Geddes, C. D., Metal-enhanced fluorescence from plastic substrates. *Journal of Fluorescence* 2005, 15, (2), 99-104.
39. Aslan, K.; Leonenko, Z.; Lakowicz, J. R.; Geddes, C. D., Annealed silver-island films for applications in metal-enhanced fluorescence: Interpretation in terms of radiating plasmons. *Journal of Fluorescence* 2005, 15, (5), 643-654.
40. Lakowicz, J. R., Radiative decay engineering 5: metal-enhanced fluorescence and plasmon emission. *Analytical Biochemistry* 2005, 337, (2), 171-194.
41. Drexhage, K. H., Influence of a dielectric interface on fluorescence decay time. *J. Luminesc* 1970, 1/2, 693-701.
42. Kummerlen, J.; Leitner, A.; Brunner, H.; Aussenegg, F. R.; Wokaun, A., Enhanced Dye Fluorescence over Silver Island Films—Analysis of the Distance Dependence. *Molecular Physics* 1993, 80, (5), 1031-1046.

The invention claimed is:

1. A metallic structure for use in a detection system to determine a ligand of interest comprising:
    a substrate fabricated from a material selected from the group consisting of glass, cellulosic material and polymeric material;
    a first and second metallic layer with a metal oxide layer positioned therebetween, wherein the metal oxide layer has a thickness from about 5 nm to 10 nm, wherein the first and second metallic layers fabricated from silver, gold, platinum, aluminum, copper, zinc, chromium, nickel, tin, iron, palladium or composites thereof and wherein the first and second metallic layers comprise metallic particles having a geometric shape selected from a triangle, square, sphere, oblong, elliptical, or rectangle and having a thickness from 25 nm to about 1000 nm, wherein the first metallic layer is positioned on the substrate; and
    a receptor molecule positioned on the second metallic layer and having affinity for the ligand of interest, and wherein binding of the ligand of interest to the receptor molecule positions an excitable molecule, that is attached to the ligand of interest, in a range from about 5 nm to 30 nm from the first metallic layer.

2. The metallic structure of claim 1, wherein the first and second metallic layers are fabricated from two distinctly different metals.

3. The metallic structure of claim 1, wherein the metal oxide layer is selected from the group consisting of $SiO_2$, $TiO_2$, $Fe_2O_3$, $CuO$, $ZnO$, $Y_2O_3$, $ZrO_2$, $Nb_2O_5$, $MoO_3$, $In_2O_3$, $SnO_2$, $Sb_2O_5$, $Ta_2O_5$, $WO_3$, $PbO$, $Al_2O_3$, and $Bi_2O_3$.

4. The metallic structure of claim 1, wherein the excitable molecule is selected from the group consisting of an intrinsic fluorophore, extrinsic fluorophore, fluorescent dye, and luminophore.

* * * * *